(12) United States Patent
Hellmold et al.

(10) Patent No.: US 11,938,005 B2
(45) Date of Patent: Mar. 26, 2024

(54) SMART ABSORBENT ARTICLE AND COMPONENTS

(71) Applicants: ONTEX BV, Buggenhout (BE); ONTEX GROUP NV, Erembodegem (BE)

(72) Inventors: Jens Hellmold, Beckum (DE); Alissa Idelson, Rheinbach (DE); Lisa Heirman, Buggenhout (BE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 1139 days.

(21) Appl. No.: 16/314,413

(22) PCT Filed: Jun. 13, 2018

(86) PCT No.: PCT/EP2018/065648
§ 371 (c)(1),
(2) Date: Dec. 29, 2018

(87) PCT Pub. No.: WO2018/229121
PCT Pub. Date: Dec. 20, 2018

(65) Prior Publication Data
US 2019/0167490 A1 Jun. 6, 2019

(30) Foreign Application Priority Data

Jun. 16, 2017 (EP) ..................................... 17176324
Nov. 14, 2017 (EP) ..................................... 17201652
(Continued)

(51) Int. Cl.
*A61F 13/42* (2006.01)
*A61B 5/00* (2006.01)
(Continued)

(52) U.S. Cl.
CPC ............ *A61F 13/42* (2013.01); *A61B 5/0002* (2013.01); *A61B 5/002* (2013.01); *A61B 5/202* (2013.01);
(Continued)

(58) Field of Classification Search
CPC ................ A61F 13/42; A61F 13/15699; A61F 2013/424; A61F 2013/429;
(Continued)

(56) References Cited

U.S. PATENT DOCUMENTS 2,852,026 A 9/1958 Karr
5,036,859 A * 8/1991 Brown ...................... A61F 5/48
340/573.5

(Continued)

FOREIGN PATENT DOCUMENTS

FR 2986151 A1 8/2013
GB 2174037 A 10/1986
(Continued)

OTHER PUBLICATIONS

International Search Report and Written Opinion for PCT/EP2018/065648; dated Sep. 14, 2018.
(Continued)

*Primary Examiner* — Jessica Arble
*Assistant Examiner* — Alessandro R Del Priore
(74) *Attorney, Agent, or Firm* — VIVICAR Law, PLLC

(57) ABSTRACT

A substrate suitable for incorporation into an absorbent article for automatic detection of wetness events therein, the substrate comprising a first surface capable of being arranged proximal to a body facing side of the absorbent article and a second surface opposite said first surface and capable of being arranged proximal to a garment facing side of said absorbent article, said substrate comprising a plurality of sensor tracks disposed on said first surface wherein
(Continued)

said sensor tracks are in electrical communication with a clip-on data processing module when connected at a position proximal to a first end of the substrate such to form a closed electrical circuit, typically for measuring resistance, impedance and/or capacitance therethrough, wherein the substrate comprises one or more slits and an insulating layer placed over said first surface to sandwich said sensor tracks therebetween, and a pocket is formed between said first surface and said insulating layer proximal to at least said first end, said pocket being in fluid communication with said slit(s) and arranged to retain at least a portion of said clip-on data processing module therein.

21 Claims, 19 Drawing Sheets

(30) Foreign Application Priority Data

Jun. 1, 2018 (WO) .................. PCT/EP2018/064392
Jun. 11, 2018 (WO) .................. PCT/EP2018/065406

(51) Int. Cl.
*A61B 5/20* (2006.01)
*A61F 13/15* (2006.01)
*G01N 27/12* (2006.01)

(52) U.S. Cl.
CPC ............ *A61B 5/207* (2013.01); *A61B 5/6804* (2013.01); *A61B 5/6808* (2013.01); *A61B 5/6892* (2013.01); *A61F 13/15699* (2013.01); *G01N 27/126* (2013.01); *A61B 2562/029* (2013.01); *A61B 2562/043* (2013.01); *A61B 2562/164* (2013.01); *A61F 2013/424* (2013.01); *A61F 2013/429* (2013.01)

(58) Field of Classification Search
CPC ..... A61B 13/00055; A61F 2013/00961; A61B 5/0002; A61B 5/002; A61B 5/202; A61B 5/207; A61B 5/6804; A61B 5/6808; A61B 5/6892; A61B 2562/029; A61B 2562/043; A61B 2562/164; A61B 5/6802; G01N 27/126; G01N 33/00; G01N 33/483; G01N 27/227; G01N 27/228; G08B 21/20
See application file for complete search history.

(56) References Cited

U.S. PATENT DOCUMENTS

| | | | |
|---|---|---|---|
| 5,389,093 A | 2/1995 | Howell | |
| 5,469,145 A * | 11/1995 | Johnson | A61F 13/42 340/573.5 |
| 6,200,250 B1 * | 3/2001 | Janszen | A61F 13/42 493/938 |
| 6,246,330 B1 * | 6/2001 | Nielsen | A61F 13/42 340/384.1 |
| 6,559,772 B2 * | 5/2003 | Zand | A61F 13/42 604/361 |
| 7,649,125 B2 * | 1/2010 | Ales, III | A61F 13/42 340/573.5 |
| 9,241,839 B2 * | 1/2016 | Abraham | A61F 13/42 |
| 2004/0030309 A1 * | 2/2004 | Huang | A61F 13/15585 604/361 |
| 2005/0113776 A1 | 5/2005 | Venturino et al. | |
| 2005/0156744 A1 | 7/2005 | Pires | |
| 2008/0057693 A1 * | 3/2008 | Tippey | A61F 13/42 438/597 |
| 2009/0292265 A1 | 11/2009 | Helmer et al. | |
| 2010/0152688 A1 * | 6/2010 | Handwerker | A61F 13/505 604/361 |
| 2010/0241094 A1 | 9/2010 | Sherron | |
| 2013/0041334 A1 | 2/2013 | Prioleau et al. | |
| 2013/0233063 A1 | 9/2013 | Wang et al. | |
| 2015/0018792 A1 | 1/2015 | Marsiquet et al. | |
| 2015/0335288 A1 * | 11/2015 | Toth | A61B 5/6833 600/391 |
| 2016/0166438 A1 * | 6/2016 | Rovaniemi | A61F 13/00059 493/320 |
| 2017/0035622 A1 | 2/2017 | Wang | |
| 2021/0151177 A1 | 5/2021 | Ohashi et al. | |
| 2022/0323263 A1 * | 10/2022 | Chen | A61F 13/42 |

FOREIGN PATENT DOCUMENTS

| | | | |
|---|---|---|---|
| JP | 2005000602 A | 1/2005 | |
| WO | 1999033037 A1 | 7/1999 | |
| WO | 2002047592 A2 | 6/2002 | |
| WO | 2002078513 A2 | 10/2002 | |
| WO | 2002101679 A1 | 12/2002 | |
| WO | WO-02101679 A1 * | 12/2002 | ............ A61F 13/42 |
| WO | 2004028403 A2 | 4/2004 | |
| WO | 2005030084 A2 | 4/2005 | |
| WO | 2008026120 A2 | 3/2008 | |
| WO | 2018229118 A2 | 12/2018 | |

OTHER PUBLICATIONS

Kirchmeyer, S. et al., "Scientific Importance, Properties and Growing Applications of Poly(3,4-Ethylenedioxythiophene)," J. Mater. Chem., 15 (21):2077-2088 (2005).

* cited by examiner

FIG.6A
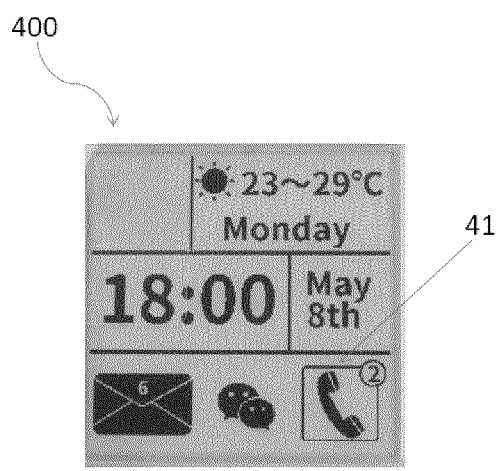
FIG.6B
| Protection Layer | ~ 40 |
| Electronic Ink | ~ 42 |
| Activation Grid | ~ 44 |
FIG.6C

SMART ABSORBENT ARTICLE AND COMPONENTS

CROSS-REFERENCE TO RELATED APPLICATIONS

This application is the national stage application of corresponding international application number PCT/EP2018/065648, filed Jun. 13, 2018, which claims priority to and the benefit of European application no. 17176324.6, filed Jun. 16, 2017, European application no. 17201652.9, filed Nov. 14, 2017, International application no. PCT/EP2018/064392, filed Jun. 1, 2018, and International application no. PCT/EP2018/065406, filed Jun. 11, 2018, all of which are hereby incorporated by reference in their entirety.

TECHNICAL FIELD

The invention pertains to the technical field of absorbent hygiene products. In particular, the present invention relates to an absorbent article for absorbing body fluids and exudates, such as urine and fecal material. More particularly, the present invention relates to absorbent garments, such as disposable diapers or pants for example for babies or adults, which are configured to collect and contain fecal material and avoid leakage.

Most particularly the invention pertains to diapers or pants, components thereof, and process of making, comprising an exudate detection system capable of automatically providing a warning to a care giver when the risk of leakage is elevated and the diaper or pant warn by a subject should be replaced.

BACKGROUND

Disposable diapers conventionally include a chassis having a liquid permeable topsheet, a liquid impermeable backsheet and an absorbent structure sandwiched between the topsheet and backsheet. The chassis has a front body panel which, in use, extends over the stomach and front hip area of the user, and a rear body panel which, in use, extends over the back and the rear hip area of the user. Each of the body panels has a waist portion such that, when the diaper is fastened around the waist of the user, the waist portions provide a continuous encirclement of the user. In order to fasten the diaper around the waist of a user, a fastening system comprising fastening tabs is commonly employed. Fastening tabs may be provided on side panels which extend from lateral side edges of the diaper chassis.

Disposable pants have a similar construction but typically comprise front and back elasticized belts at either end of the absorbent structure and are sealed together at lateral side seams to form an underwear-resembling product that can be worn by a subject by pulling it up over the legs and may be removed either by pulling it down in the opposite direction or by tearing the side seams.

Inherent with the use of such absorbent articles, eventually one or more wetness and/or exudate events will occur and thus a need for change of the absorbent article arises. Particularly in home care and/or institutions, handling elderly with incontinence problems, knowing when to change the diaper/pant of a patient is important. Indeed, changing the diapers too early results in unnecessary cost and waste and changing too late results in further cleaning costs and time, and uncomfort or discomfort to the patient. This problem is exacerbated by motion, indeed taking into account that a subject wearing the article may move into different positions the saturation thereof and/or risk of leakage may vary considerably based on the position and time the subject remains in that position during and/or after one or more wetness/exudate events.

Absorbent articles possessing different types of detecting means are known, and help to alert a user or caregiver to a change within the article (e.g. a soiling event). Such detecting means allow the user or caregiver to readily determine whether or not an absorbent article needs to be changed, without the need for close inspection or removal of the article.

Commonly known detecting means which can be incorporated into absorbent articles are chemical substances which alter their form or nature upon contact with liquid. For example, an indication that an absorbent article is soiled can arise from colour changes or the appearance or disappearance of an element on the absorbent article. Such technology is known from, e.g. U.S. Pat. No. 5,389,093, WO 04/028403 and WO 05/030084. Such detecting means are useful in certain situations, but less so in institutions such as childcare centres, care centres for the elderly or hospitals where the status of a large number of wearers must be monitored, often by a limited staff. Determining whether the absorbent article is soiled or not still requires the wearer to be disturbed, as the coloured element must still be visible to the caregiver. This often requires that the wearer be moved, and their clothes removed or adjusted.

WO02/47592 describes an article having a status signalling device for communicating a change in status of a monitored portion. The signalling device can comprise a sensor located within the article, the sensor being connected to an external portion located on the outside of the article. Changes in the status of the article (e.g. soiling) can be transmitted from the signalling device to a receiver via an RF link produced by the external portion. The external portion is included on the outside of the article and is secured in place, e.g. by hook-and-loop type fasteners. As such, it can be removed or displaced and is subject to external influences (e.g. abrasion, moisture, interference by the wearer). Furthermore, traditional components of the external portion described in WO02/47592 render it comparatively expensive to produce, which in turn, renders its disposal expensive and reuse more likely.

US 2005/0156744 describes a diaper similar to that of WO02/47592, in which a detachable transmitter is installed on the outside of the diaper.

WO02/78513 describes a fluid discharge monitoring apparatus for a diaper. The apparatus comprises an RF tag which is responsive to the discharge of fluid into the diaper. There is no discussion in WO02/78513 as to the nature of the components which are used in the fabrication of the monitoring apparatus.

JP 2005000602 describes a wet detecting device in a diaper, comprising an RF-ID tag. The tag comprises an IC chip, a communication control section, data storage medium and an antenna.

WO 99/33037 discloses a method and apparatus for detecting a fluid, said method comprising providing one or more oscillators transmitting electromagnetic energy, providing one or more resonant circuits receiving electromagnetic energy from the oscillators, bringing the fluid and the one or more resonant circuits into contact with each other so that the receptions of the electro-magnetic energy of the resonant circuits are changed, and detecting changes of the transmissions of electromagnetic energy of the oscillators by changes in one or more characteristics thereof upon the changes in the receptions of the electromagnetic energy of the resonant circuits. The resonant circuits may consist of coils having separated windings made of an electrically conducting material, which may be provided by printing on a substrate. The resonant circuit(s) may be embedded in a diaper. Thus, WO 99/33037 discloses an absorbent article comprising at least one wetness detecting means.

Although electrical detecting means for indicating the status of an absorbent article have clear advantages over visual detecting means, they still suffer from the drawbacks of being expensive, stiff, bulky and difficult to incorporate into the article during manufacture. In addition, many traditional electrical components are not readily disposable or degradable. Traditional components of electrical circuits such as soldered metal are not compatible with materials such as paper, plastics and fibrous materials used in modern absorbent articles. Neither are they compatible with the rapid assembly-line manufacturing methods used in the production of absorbent articles. As absorbent articles are primarily intended for single use (i.e. they are disposable), it would be a great advantage if electrical detecting means were cheap and readily disposable. There is thus a desire for a detecting means which can be readily incorporated into an absorbent article which provides the advantages of electrical detection, yet which is cost-effective, simple to manufacture and readily disposable.

There is also a desire for absorbent articles comprising detecting means that provide accurate and reliable sensing and that can be standardized across a range of products and sizes in order to limit production cost and thus the end cost to the users and institutions.

There is further a desire for detections means that further take into account not only warning when exudate events happen, but alternatively or in combination provide on-time alerts based on the risk of exudate leakage from the absorbent article, for example taking into account the position that the subject is in during and/or after one or more repeated wetness/exudate events.

SUMMARY OF THE INVENTION

In a first aspect, the disclosure relates to a substrate suitable for incorporation into an absorbent article for automatic detection of wetness events therein, the substrate comprising a first surface capable of being arranged proximal to a body facing side of the absorbent article and a second surface opposite said first surface and capable of being arranged proximal to a garment facing side of said absorbent article, said substrate comprising a plurality of sensor tracks disposed on said first surface wherein said sensor tracks are in electrical communication with a clip-on data processing module when connected at a position proximal to a first end of the substrate such to form a closed electrical circuit, typically for measuring resistance, impedance and/or capacitance therethrough, wherein the substrate comprises one or more slits and an insulating layer placed over said first surface to sandwich said sensor tracks therebetween, and a pocket is formed between said first surface and said insulating layer at least proximal to said first end, said pocket being in fluid communication, preferably only, with said slit(s) and arranged to retain at least a portion of said clip-on data processing module therein.

In a further aspect, the disclosure relates to a substrate suitable for incorporation into an absorbent article for automatic detection of wetness events therein, the substrate comprising a first surface capable of being arranged proximal to a body facing side of the absorbent article and a second surface opposite said first surface and capable of being arranged proximal to a garment facing side of said absorbent article, said substrate comprising a plurality of sensor tracks disposed on said first surface and said sensor tracks comprising: at least one central track extending parallel to a length of the substrate and parallel to a longitudinal axis crossing a first end and a second end of the substrate; at least two side tracks extending parallel to the central track and oppositely arranged such that the central track extends therebetween; and wetness sensing tracks extending outboard of said two side tracks, wherein said central track, said side tracks, and said wetness sensing tracks are in electrical communication via one or more shortening elements positioned proximal to said second end and distal from said first end, and wherein the substrate is connectable to a clip-on data processing module at a position proximal to said first end and distal from said shortening elements such to form a closed electrical circuit, typically for measuring resistance and/or capacitance therethrough. In an embodiment said substrate consists of a liquid impermeable backsheet, preferably a breathable liquid impermeable backsheet.

In a second aspect, the disclosure relates to an absorbent article, preferably a disposable diaper or pant, suitable for detecting a wetness event therein and/or risk of exudate leakage therefrom, said absorbent article comprising: a liquid impermeable backsheet; a liquid permeable topsheet; and an absorbent core interposed between said backsheet and topsheet, wherein said backsheet comprises a substrate, the substrate comprising: a plurality of sensor tracks disposed on said first surface and said sensor tracks comprising: at least one central track extending parallel to a length of the substrate and parallel to a longitudinal axis crossing a first end and a second end of the substrate; at least two side tracks extending parallel to the central track and oppositely arranged such that the central track extends therebetween; and wetness sensing tracks extending outboard of said two side tracks, wherein said central track, said side tracks, and said wetness sensing tracks are in electrical communication via one or more shortening elements positioned proximal to said second end and distal from said first end, and wherein the substrate is connectable to a clip-on data processing module at a position proximal to said first end and distal from said shortening elements such to form a closed electrical circuit, typically for measuring resistance and/or capacitance therethrough.

In a third aspect, the disclosure relates to a process of making an absorbent article comprising the steps of: providing a liquid impermeable backsheet and applying a plurality of sensor tracks, said sensor tracks comprising at least one central track extending parallel to a length of the substrate and parallel to a longitudinal axis crossing a first end and a second end of the substrate; at least two side tracks extending parallel to the central track and oppositely arranged such that the central track extends therebetween; and wetness sensing tracks extending outboard of said two side tracks, wherein said central track, said side tracks, and said wetness sensing tracks are in electrical communication via one or more shortening elements positioned proximal to said second end and distal from said first end, and wherein the substrate is connectable to a clip-on data processing module at a position proximal to said first end and distal from said shortening elements such to form a closed electrical circuit, typically for measuring resistance and/or capacitance therethrough; providing an insulating layer having a width, taken along an axis perpendicular to the longitudinal axis, being less than a width of said backsheet, and optionally applying one or more shortening elements thereto, optionally further applying one or more secondary shortening elements thereto; adhering said insulating layer to said backsheet, said insulating layer being sized and positioned to cover the at least one central track and the at least two side tracks, to provide a laminated substrate; providing an absorbent core comprising absorbent material; providing a liquid permeable topsheet; and sandwiching the absorbent core between said backsheet and said topsheet.

In a further aspect, the disclosure relates to a process of making an absorbent article comprising the steps of: providing a first continuous film and applying a plurality of sensor tracks, said sensor tracks comprising at least one central track extending parallel to a length of the substrate and parallel to a longitudinal axis crossing a first end and a second end of the substrate; at least two side tracks extending parallel to the central track and oppositely arranged such that the central track extends therebetween; and wetness sensing tracks extending outboard of said two side tracks, wherein said central track, said side tracks, and said wetness sensing tracks are in electrical communication via one or more shortening elements positioned proximal to said second end and distal from said first end, and wherein the substrate is connectable to a clip-on data processing module at a position proximal to said first end and distal from said shortening elements such to form a closed electrical circuit, typically for measuring resistance and/or capacitance therethrough; providing a second continuous film having a width, taken along an axis perpendicular to the longitudinal axis, being less than a width of said first continuous film, and optionally applying one or more shortening elements thereto, optionally further applying one or more secondary shortening elements thereto; adhering said second continuous film to said first continuous film, said second continuous film being sized and positioned to cover the at least one central track and at least a portion of the at least two side tracks (typically said "at least portion" being proximal to a position where the clip-on data processing module is connected to said substrate), to provide a laminated substrate; providing an absorbent core comprising absorbent material and a liquid permeable topsheet; and sandwiching the absorbent core between said laminated substrate and said topsheet, to form a laminated assembly; optionally cutting said laminated assembly at regular intervals to form a plurality of individual absorbent articles.

In a further aspect, the disclosure relates to a clip-on data processing module suitable for removable attachment to an absorbent article for automatic detection of wetness events therein, the module comprising: a housing; and a flexible connection member (though it is understood herein that a stiff connection member may equally be used as long as mechanically suitable for, for example, clamping, albeit a flexible connection may provide some advantages as will be described herein below) coupled to said housing and having a free end being cantilevered from said housing, said end comprising one or more electrically conducting connection ports, wherein the housing comprises therein a data processing system, said data processing system comprising a power source, a processor, and a transmitter; and a motion sensor in electrical communication with at least said processor, the flexible connection member being arranged to fasten to a surface of the absorbent article, wherein the absorbent article comprises a plurality of sensor tracks, and to electrically connect at least two of said plurality of sensor tracks to said processing system via said one or more electrically conducting connection ports.

In a further aspect, the disclosure relates to a kit of parts comprising a clip-on data processing module as described herein above; and an absorbent article as described herein above, and optionally a charging unit adapted to charge a plurality of clip-on data processing modules at a given time, preferably via wireless charging.

In a further aspect, the disclosure relates to a clip-on data processing module suitable for removable attachment to an absorbent article for automatic detection of wetness events therein, the module comprising: a housing; and a flexible connection member coupled to said housing and having a free end being cantilevered from said housing, said end comprising one or more electrically conducting connection ports, wherein the housing and/or said flexible connection member comprises therein a data processing system, said data processing system comprising a power source, a processor, and a transmitter; and a motion (or position) sensor in electrical communication with at least said processor, the flexible connection member being arranged to fasten to a surface of the absorbent article, and to electrically connect at least one, preferably at least two, of a plurality of sensor tracks present on a body facing side of a backsheet of said absorbent article, to said processing system via said one or more electrically conducting connection ports, and wherein said housing further comprises an electronic-ink (although preferred due to its lower power consumption, alternative displays may also be considered herein such as LCD) based display for displaying textual and/or graphical indicia, said display comprising: a layer of electronic ink including a bi-stable non-volatile imaging material disposed between an activation layer and a transparent electrode layer located above the layer of electronic ink, for activating the layer of electronic ink at particular locations to display textual and/or graphical indicia on the surface of the display, wherein the layer of electronic ink does not require electrical power to maintain the indicia visible.

In a further aspect, the disclosure relates to a substrate suitable for incorporation into an absorbent article for automatic detection of wetness events therein, the substrate comprising a first surface capable of being arranged proximal to a body facing side of the absorbent article and a second surface opposite said first surface and capable of being arranged proximal to a garment facing side of said absorbent article, said substrate comprising a plurality of sensor tracks disposed on said first surface and said sensor tracks comprising: at least two side tracks extending parallel to a length of the substrate proximal to a first and second side edge of the substrate respectively, the side edges extending parallel to the longitudinal axis and between first and second ends thereof; wetness sensing tracks extending between said two side tracks, wherein said two side tracks each have one free end proximal to said first end of the substrate and one connected end being in electrical communication with said wetness sensing tracks, and wherein the substrate is connectable to a clip-on data processing module at a position proximal to said first end such to form a closed electrical circuit, typically for measuring resistance and/or capacitance therethrough. In an embodiment, the two side tracks are feedback tracks. In an embodiment said substrate consists of a liquid impermeable backsheet, preferably a breathable liquid impermeable backsheet.

In a further aspect the disclosure relates to a substrate suitable for incorporation into an absorbent article for automatic detection of wetness events therein, the substrate comprising a first surface capable of being arranged proximal to a body facing side of the absorbent article and a second surface opposite said first surface and capable of being arranged proximal to a garment facing side of said absorbent article, said substrate comprising a plurality of sensor tracks disposed on said first surface and said sensor tracks comprising: at least one central track extending parallel to a length of the substrate and parallel to a longitudinal axis, said axis crossing a first end and a second end of the substrate; at least two side tracks extending parallel to the central track for only a portion thereof over said length (said portion preferably being at a location of connection to the data processing module) and oppositely arranged such that the central track extends substantially therebetween, or linearly displaced along the longitudinal axis such that the central track is laterally spaced therefrom along said longitudinal axis; and wetness sensing tracks extending outboard of said two side tracks and/or central track, wherein said central track, said side tracks, and said wetness sensing tracks are in electrical communication via one or more shortening elements positioned proximal to said second end and distal from said first end, and wherein the substrate is connectable to a data processing module, that may be integral to the substrate or a clip-on, at a position proximal to said first end and distal from said shortening elements such to form a closed electrical circuit, typically for measuring resistance and/or capacitance therethrough. In an embodiment said substrate consists of a liquid impermeable backsheet, preferably a breathable liquid impermeable backsheet.

DESCRIPTION OF FIGURES

FIG. 6A-C illustrate an exemplary embodiment of a clip-on module according to the present disclosure.

DETAILED DESCRIPTION OF THE INVENTION

Figure 1A:
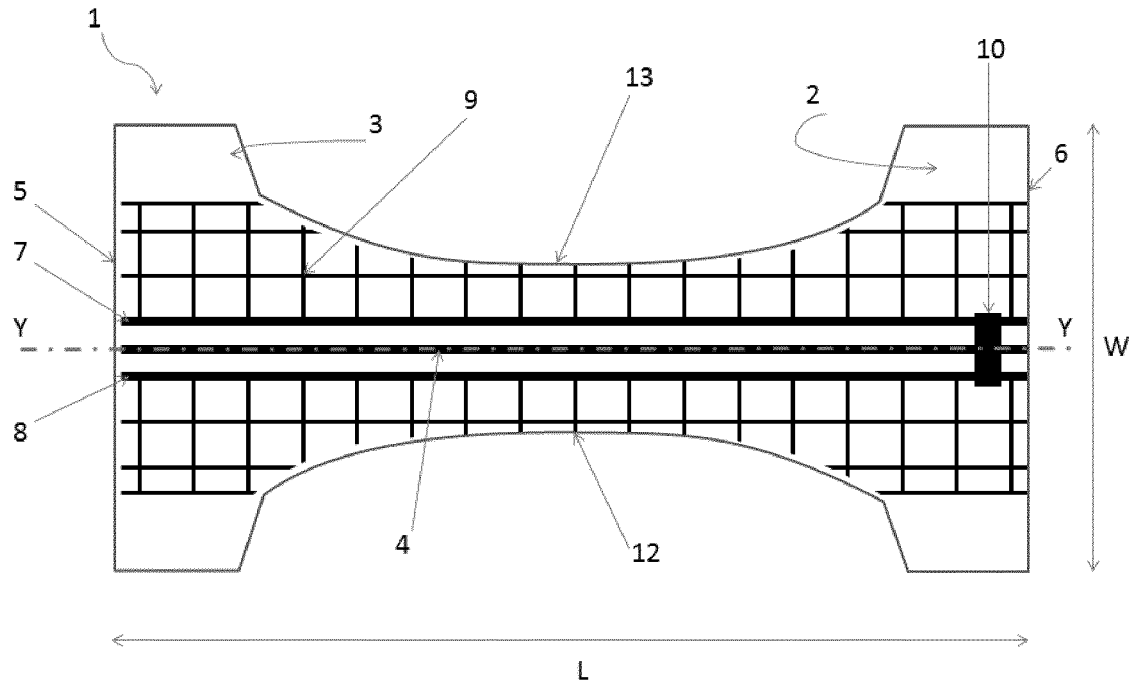
FIG. 1A illustrates a top view schematic of substrate according to an embodiment of the disclosure.
Figure 1B:
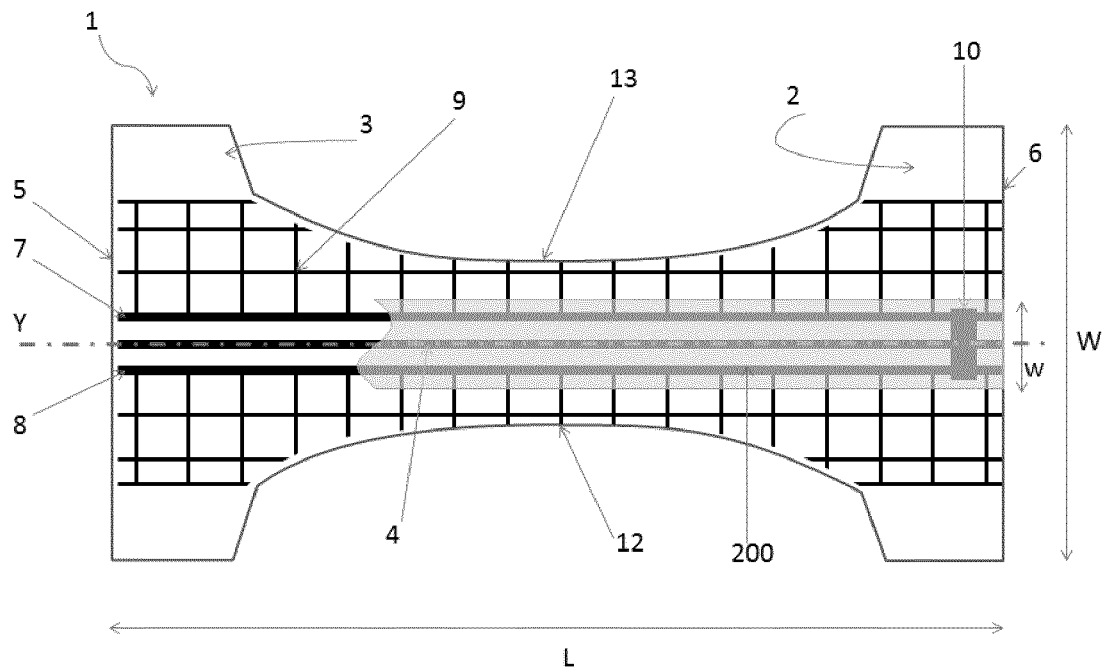
FIG. 1B illustrates a top view schematic of substrate according to an embodiment of the disclosure.
Figure 2A:
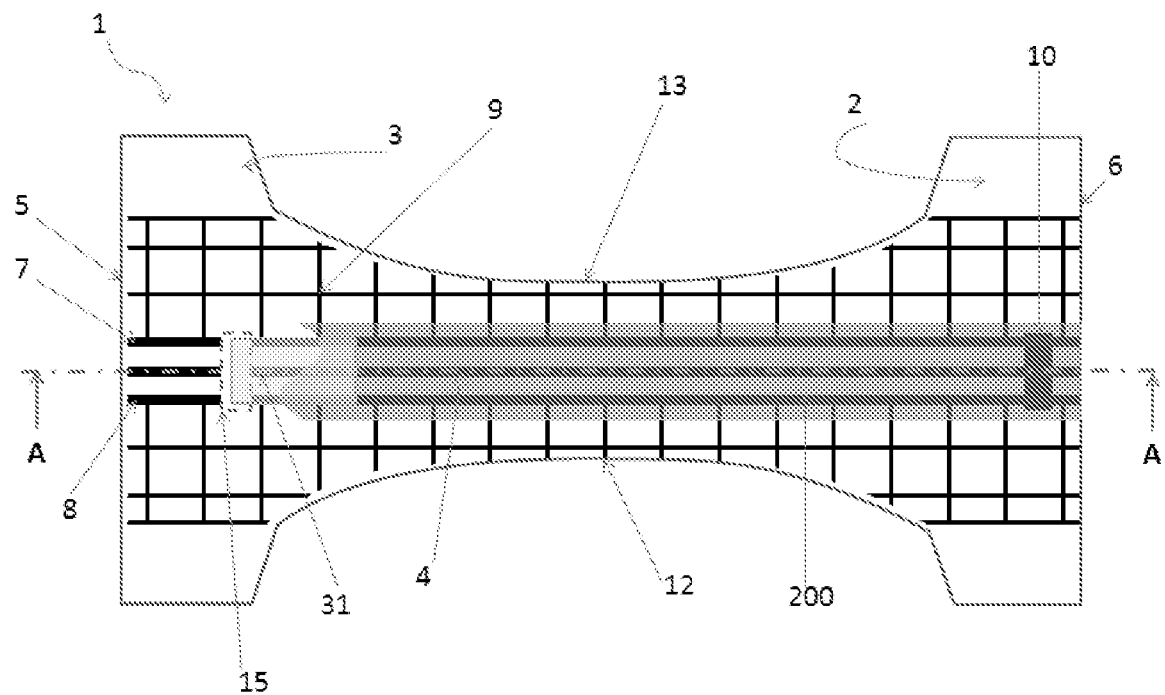
FIG. 2A illustrates a top view schematic of substrate according to an embodiment of the disclosure.
Figure 2B:
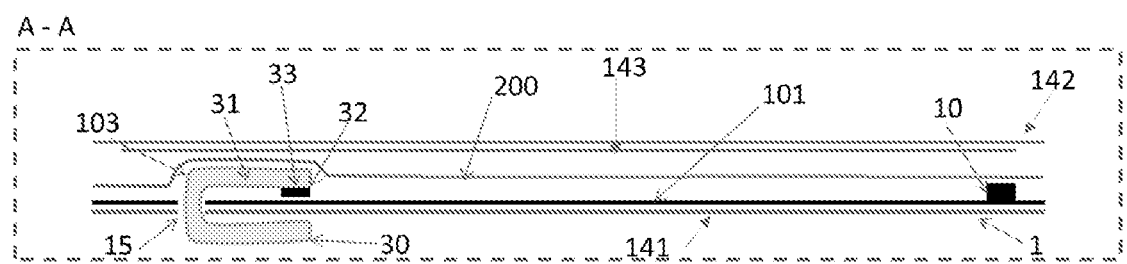
FIG. 2B illustrates a cross-sectional schematic of the substrate of FIG. 2A about axis A-A.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed. "Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation or element referred to.

The recitation of numerical ranges by endpoints includes all numbers and fractions subsumed within that range, as well as the recited endpoints, except where otherwise explicitly stated by disclaimer and the like.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious top sheet, a back sheet joined to the top sheet, and an absorbent core positioned and held between the top sheet and the back sheet. The top sheet is operatively permeable to the liquids that are intended to be held or stored by the absorbent article, and the back sheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface. Preferably, a diaper comprises a liquid permeable "top sheet", a liquid impermeable "back sheet", and an "absorbent medium or core" disposed between the top sheet and the back sheet. The top sheet, back sheet and the absorbent medium could be made from any suitable material known to the person skilled in the art. The top sheet is generally located at or near the bodyside surface of the article, while the back sheet is generally located at or near the garment-side surface of the article. Optionally, the article may comprise one or more separate layers which are in addition to the back sheet and are interposed between the back sheet and the absorbent medium. Top sheet and back sheet are connected or otherwise associated together in an operable manner.

The "absorbent medium" or "absorbent core" or "absorbent body" is the absorbent structure disposed between the top sheet and the back sheet of the absorbent article in at least the crotch region of the absorbent article and is capable of absorbing and retaining liquid body exudates. The size and the absorbent capacity of the absorbent medium should be compatible with the size of the intended wearer and the liquid loading imparted by the intended use of the absorbent article. Further, the size and the absorbent capacity of the absorbent medium can be varied to accommodate wearers ranging from infants through adults. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material.

"Registered" (e.g. Registered design) refers to, for example, a print design that varies along the length of a continuous web/film (and is repeated at intervals throughout) and that hence requires some form of recognition on where a processing action must happen, e.g. a cut, to ensure that consecutive discrete products formed from the continuous web/film each have the same print design.

"Acquisition and distribution layer", "ADL" or "surge management portion" refers to a sub-layer which preferably is a nonwoven wicking layer under the top sheet of an absorbent product, which speeds up the transport and improves distribution of fluids throughout the absorbent core. The surge management portion is typically less hydrophilic than the retention portion, and has the ability to quickly collect and temporarily hold liquid surges, and to transport the liquid from its initial entrance point to other parts of the absorbent structure, particularly the retention portion. This configuration can help prevent the liquid from pooling and collecting on the portion of the absorbent garment positioned against the wearer's skin, thereby reducing the feeling of wetness by the wearer. Preferably, the surge management portion is positioned between the top sheet and the retention portion.

The term "adhesive" as used herein is intended to refer to any suitable hot melt, water or solvent borne adhesive that can be applied to a surface of a film layer in the required pattern or network of adhesive areas to form the film-nonwoven laminate of the present invention. Accordingly, suitable adhesives include conventional hot melt adhesives, pressure-sensitive adhesives and reactive adhesives (i.e., polyurethane). As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein, the term "associated or joined or adhered" encompasses, unless expressly stated, configurations in which e.g. a top sheet is directly joined to a back sheet by affixing the top sheet directly to the back sheet, and also configurations wherein the top sheet is joined to the back sheet by affixing the top sheet to intermediate members which in turn are affixed to the back sheet (i.e. indirectly joining). Top sheet and back sheet can be affixed directly to each other by attachment means such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix top sheet to back sheet. It should be readily appreciated that the above-described attachment means may also be employed to interconnect and assemble together the various other component parts of the article described herein.

The terms "back section" and "rear back section" are used herein as synonyms and refer to the area of the absorbent article which is contact with the back of the wearer when the absorbent article is worn.

The term "backsheet" refers to a material forming a liquid impermeable cover of the absorbent article. The back sheet prevents the exudates contained in the absorbent structure from wetting articles such as bedsheets and overgarments which contact the disposable absorbent article. The back sheet may be a unitary layer of material or may be a composite layer composed of multiple components assembled side-by-side or laminated. The back sheet may be the same or different in different parts of the absorbent article. At least in the area of the absorbent medium the back sheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The back sheet material may be breathable so as to allow vapour to escape from the absorbent material, while still preventing liquids from passing there through. Examples of breathable back sheet materials are porous polymeric films, nonwoven laminates of spunbond and meltblown layers and laminates of porous polymeric films and nonwoven materials.

The terms "belly section" and "front belly section" are used herein as synonyms and refer to the area of the absorbent article which is contact with the belly of the wearer when the absorbent article is worn.

As used herein, the "body-facing" or "bodyside" surface means that surface of the article or component which is intended to be disposed toward or placed adjacent to the body of the wearer during ordinary use, while the "outward", "outward-facing" or "garment-side" surface is on the opposite side, and is intended to be disposed to face away from the wearer's body during ordinary use. Such outward surface may be arranged to face toward or placed adjacent to the wearer's undergarments when the absorbent article is worn.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

The term "breathable" refers to layers, preferably films or elastic laminates, having a water vapor transmission rate (WVTR) of at least 300 grams/m$^2$-24 hours.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

Further, an absorbent article can comprise "containment flaps" or "barrier cuffs". The containment flaps are generally thought to be particularly well suited for the containment of fecal matter and to prevent the lateral flow of liquid waste until such time as the liquid waste can be absorbed by the absorbent article. Many constructions of containment flaps are known. Such containment flaps generally comprise a proximal edge, intended to be attached to the absorbent article, and an opposite distal edge which is generally not attached to the absorbent article along at least a portion of its length. An elastic member is generally located adjacent the distal edge to assist in maintaining the containment flap in an upright condition and in maintaining a sealing relationship between the distal edge of the containment flap and the body of a wearer during use. The elastic member is generally located between two layers of material so that the elastic does not come into contact with the body of a wearer. The containment flaps may be manufactured from a wide variety of materials such as polypropylene, polyester, rayon, nylon, foams, plastic films, formed films, and elastic foams. A number of manufacturing techniques may be used to manufacture the containment flaps. For example, the containment flaps may be woven, non-woven, spunbonded, carded, cast, blown or the like.

An absorbent article can comprise leg containment gaskets. Leg "containment gaskets" help prevent leakage of bodily exudates when the wearer exerts compressive forces on the absorbent article. In particular, the stiffness of the leg containment gaskets prevents twisting and bunching of the leg openings of the absorbent article which can lead to leaks. In addition, the elasticity and conformability of the leg containment gaskets ensures that the bodyfacing surface of the leg containment gaskets provides an adequate seal against the body of the wearer. The physical properties of the leg containment gaskets, such as the thickness and stiffness, also function to space the bodyside liner, outer cover and absorbent core away from the wearer's body when in use. As such, void volume is created between the wearer's body and the bodyside liner and absorbent core of the absorbent article to help contain body exudates.

"Mechanical bond" is an attachment between two or more elements, components, regions, or webs and may comprise heat bonds, pressure bonds, ultrasonic bonds, dynamic mechanical bonds, or any other suitable non-adhesive attachment means or combinations of these attachment means.

"Hotmelt adhesive" means a formulation that generally comprises several components. These components typically include one or more polymers to provide cohesive strength (e.g., aliphatic polyolefins such as poly (ethylene-co-propylene) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers. For example, a typical hot-melt adhesive formulation might contain from about 15 to about 35 weight percent cohesive strength polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive formulations comprising different weight percentages of these components are possible.

"Discontinuous bonding pattern" as used herein refers to a pattern of bonding areas, in particular bonding areas between layers, whereby at least in at least one region the layers are not bonded. A discontinuous bonding pattern may comprise a connected bonding area or multiple disconnected bonding areas. A discontinuous bonding pattern further may comprise a connected bonding area comprising a number of holes, where the layers are not bonded, preferably according to a regular pattern, or it may comprise discrete disconnected bonding areas, e.g. a point bonded pattern which comprises a plurality of separate bonding points surrounded by unbonded areas or a line-bonded pattern which comprises a plurality of separate bonding lines alternated by unbonded areas, preferably according to a regular pattern. The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the terms "elastic", "elastomeric", "elasticity" or derivations thereof are used to describe the ability of various materials and objects comprised of such to reversibly undergo deformation under stress, e.g., become stretched or extended, in at least one direction when a force is applied to the material and to resume substantially to their original dimensions upon relaxing, i.e., when the force is released, without rupture or breakage. Preferably, it refers to a material or composite which can be elongated in at least one direction by at least 50% of its relaxed length, i.e., elongated to at least 150% of its relaxed length, and which will recover upon release of the applied tension at least 40% of its elongation. Accordingly, upon release of the applied tension at 50% elongation, the material or composite contracts to a relaxed length of not more than 130% of its original length. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

The term "elasticized" or "elastified" refers to a material, layer, or substrate that is naturally non-elastic, but which has been rendered elastic by, for example, suitably joining an elastic material, layer, or substrate thereto.

"Elongation" means the ratio of the extension of a material to the length of the material prior to the extension (expressed in percent). "Extension" means the change in length of a material due to stretching (expressed in units of length).

As used herein the term "extensible" means elongatable in at least one direction, but not necessarily recoverable.

The term "finished" or "final", when used with reference to a product, means that the product has been suitably manufactured for its intended purpose.

As used herein, the term "garment" means any type of apparel which may be worn. This includes diapers, training pants, incontinence products, surgical gowns, industrial workwear and coveralls, undergarments, pants, shirts, jackets and the like.

The term "graphic" includes, but is not limited to, any type of design, image, mark, figure, codes, words, patterns, or the like. For a product such as a training pant, graphics will generally include objects associated with little boys and little girls, such as multi-color trucks, airplanes, balls, dolls, bows, or the like.

As used herein, the term "impermeable" generally refers to articles and/or elements that are substantially not penetrated by aqueous fluid through the entire thickness thereof under a pressure of 1.0 kPa or less. Preferably, the impermeable article or element is not penetrated by aqueous fluid under pressures of 3.4 kPa or less. More preferably, the impermeable article or element is not penetrated by fluid under pressures of 6.8 kPa or less. An article or element that is not impermeable is permeable.

"Integral" is used to refer to various portions of a single unitary element rather than separate structures bonded to or placed with or placed near one another.

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

The term "laid-flat state" or "fully stretched state" or "extended state" is intended to refer to the article when it is flattened into a plane or is substantially flattened into a plane and is used in contrast to when the article otherwise positioned, such as when the article is folded or shaped in or for use by a wearer.

The use of the term "layer" can refer, but is not limited, to any type of substrate, such as a woven web, nonwoven web, films, laminates, composites, elastomeric materials, or the like, or even formulations, such as adhesives, that form a substrate upon a change in conditions (e.g. solidification of a hotmelt adhesive when the temperature drops below a predetermined amount). A layer can be liquid and air permeable, permeable to air but impermeable to liquids, impermeable both to air and liquid, or the like. When used in the singular, it can have the dual meaning of a single element or a plurality of elements.

The term "nonwoven fabric or web" means a sheet material having a structure of individual fibers or threads which are interlaid, but not in a regular manner such as occurs with knitting or weaving processes. Nonwoven fabrics or webs have been formed from many processes such as for example, meltblowing processes, spunbonding processes, and bonded carded web processes.

By the terms "particle", "particles", "particulate", "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

Use of the term "substrate" includes, but is not limited to, woven or nonwoven webs, porous films, ink permeable films, paper, composite structures, or the like.

Superabsorbent materials (e.g. superabsorbent polymers) suitable for use in the present disclosure are known to those skilled in the art, and may be in any operative form, such as particulate form, fibers and mixtures thereof. Generally stated, the "superabsorbent material" can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. The superabsorbent material may suitably be included in an appointed storage or retention portion of the absorbent system, and may optionally be employed in other components or portions of the absorbent article. The superabsorbent material may be included in the absorbent layer or other fluid storage layer of the absorbent article of the present invention in an amount up to about 60% by weight. Typically, the superabsorbent material, when present, will be included in an amount of about 10% to about 100% by weight, based on the total weight of the absorbent layer.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 µm, preferably between 300 to 600 µm, more preferably between 400 to 500 µm.

The term "topsheet" refers to a liquid permeable material sheet forming the inner cover of the absorbent article and which in use is placed in direct contact with the skin of the wearer. The top sheet is typically employed to help isolate the wearer's skin from liquids held in the absorbent structure. The top sheet can comprise a nonwoven material, e.g. spunbond, meltblown, carded, hydroentangled, wetlaid etc. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. The top sheet material may further be composed of two fibres, which may be bonded to each other in a bonding pattern. Further examples of top sheet materials are porous foams, apertured plastic films, laminates of nonwoven materials and apertured plastic films etc. The materials suited as top sheet materials should be soft and non-irritating to the skin and be readily penetrated by body fluid, e.g. urine or menstrual fluid. The inner coversheet may further be different in different parts of the absorbent article. The top sheet fabrics may be composed of a substantially hydrophobic material, and the hydrophobic material may optionally be treated with a surfactant or otherwise processed to impart a desired level of wettability and hydrophilicity.

As used herein, the term "transverse" or "lateral" refers to a line, axis, or direction which lies within the plane of the absorbent article and is generally perpendicular to the longitudinal direction.

"Ultrasonic welding" refers to a technology which joins two materials by melting them with heat generated from ultrasonic oscillation and then laminating them together, such that the molten materials flow and fill the gap between the two unaffected portions of the two materials, respectively. Upon cooling and shaping, the two materials are joined together.

"Form-driven locking" refers to locking via the shape of an element, such as a key lock wherein the shape of an element provides a resisting force to the opening thereof.

"Force-driven locking" refers to locking via a means selected from the group consisting of electromechanical, magnetic, adhesive and combinations thereof.

"Substantial portion" as used herein with reference to a element/component (e.g. wetness sensing tracks), refers to at least 80%, preferably at least 90%, more preferably at least 95%, of said element/component, generally measured as a surface area taken in the laid flat state of the absorbent article.

"Wetness sensing tracks" as used herein refer to tracks that are suitable for wetness sensing but are not limited thereto, for example said tracks may further or alternatively sense other form of exudates that not necessarily result in wetness, such as stool detection.

"Substantially perpendicular (or parallel)" refers to an element extending at an angle of not more than 35°, preferably less than 25°, more preferably less than 20°, even more preferably less than 15°, even more preferably less than 10°, most preferably less than 5°, from the referred perpendicular (or parallel) axis.

Embodiments according to the disclosure will now be described. It is understood that technical features described in one or more embodiments maybe combined with one or more other embodiments without departing from the intention of the disclosure and without generalization therefrom.

The Substrate

The substrate 1 is suitable for incorporation into an absorbent article 100 for automatic detection of wetness events therein and/or risk of exudate leakage therefrom, and may comprise a first surface 2 capable of being arranged proximal to a body facing side of the absorbent article 100 and a second surface 3 opposite said first surface 2 and capable of being arranged proximal to a garment facing side of said absorbent article 100, said substrate 1 typically comprising a plurality of sensor tracks 101 disposed on said first surface 2 wherein said sensor tracks 101 are in electrical communication with a clip-on data processing module 103 when connected at a position proximal to a first end 5 of the substrate 1 such to form a closed electrical circuit, typically for measuring resistance, impedance and/or capacitance therethrough, wherein said substrate 1 preferably comprises one or more slits 15 and an insulating layer 200 placed over said first surface 2 to sandwich at least a portion of (preferably said portion at least comprising the central track as will be described in more detail below) said sensor tracks 101 therebetween, and wherein a pocket 16 is formed between said first surface 2 and said insulating layer 200 at least proximal to said first end 5, said pocket 16 being in fluid communication, preferably only, with said slit(s) 15 and arranged to retain at least a portion of said clip-on data processing module 103 therein. An advantage of this arrangement is that an effective retaining pocket is attained in a cheap and scalable manufacturing process allowing for manufacturing of such substrates at high production speeds and still ensure a pocket is formed to retain the module in contact with the sensor tracks whilst at the same time providing insulation against exudates as the substrate becomes saturated.

Figure 19:
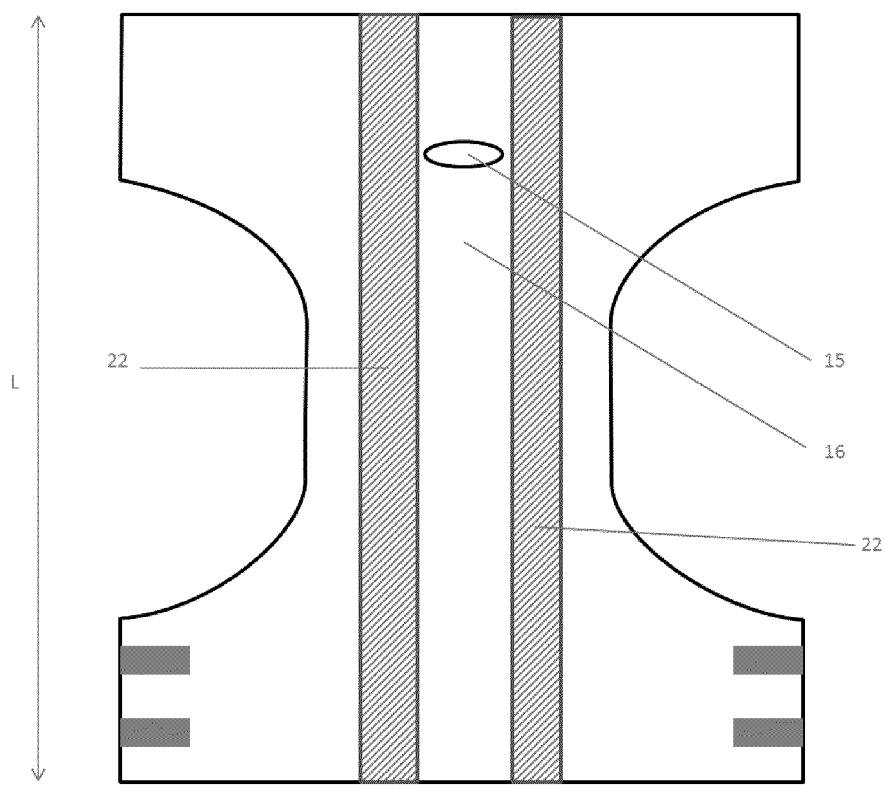
FIG. 19 is a top view schematic of a pocket and bonding arrangement according to an embodiment of the disclosure.

In an embodiment, as shown in FIG. 19, the pocket 16 is in the form of a channel extending from the first end 5 to a second end 6 of the substrate 1, preferably said channel being flanked by oppositely disposed bonding seals 22, typically such that said channel remains impermeable to exudates. Advantageously, this arrangement allows to limit inaccuracies in the sensor measurements by providing appropriate insulation to the sensor tracks that are connected to the module whilst allowing for a cheap and fast continuous production. In an embodiment, the ends of the channel proximal to the first end 5 and/or second end 6 of the substrate 1 are free of bonding seals 22. In an alternative embodiment, as shown in FIG. 9, the ends of the channel proximal to the first end 5 and/or second end 6 of the substrate 1 also comprise bonding seals 22.

Preferably the pocket 16 is sized such that it matches the dimensions of a pocket insertion member of the clip-on module 103 (sometimes also referred to herein as the connection member) that typically comprises terminals 33 (as will be described herein below in more detail), such that said terminals 33 come into electrical communication with respective portions of the sensor tracks 101 by simply inserting the clip-on module into the pocket 16 until a pocket dimension stops it from being inserted any further. Advantageously this allows the care giver to connect the clip-on module without having to worry about particularly positioning the module to ensure good electrical connection.

Preferably the pocket 16 is sized such that it accommodates at least 30%, preferably at least 50%, more preferably at least 70%, even more preferably at least 80%, of the total surface area, or total volume, of the clip-on data processing module 103 therein. An advantage is that the module may be appropriately attached and retained in a secure way and provide reduced risk of inadvertent detachment.

Figure 9:
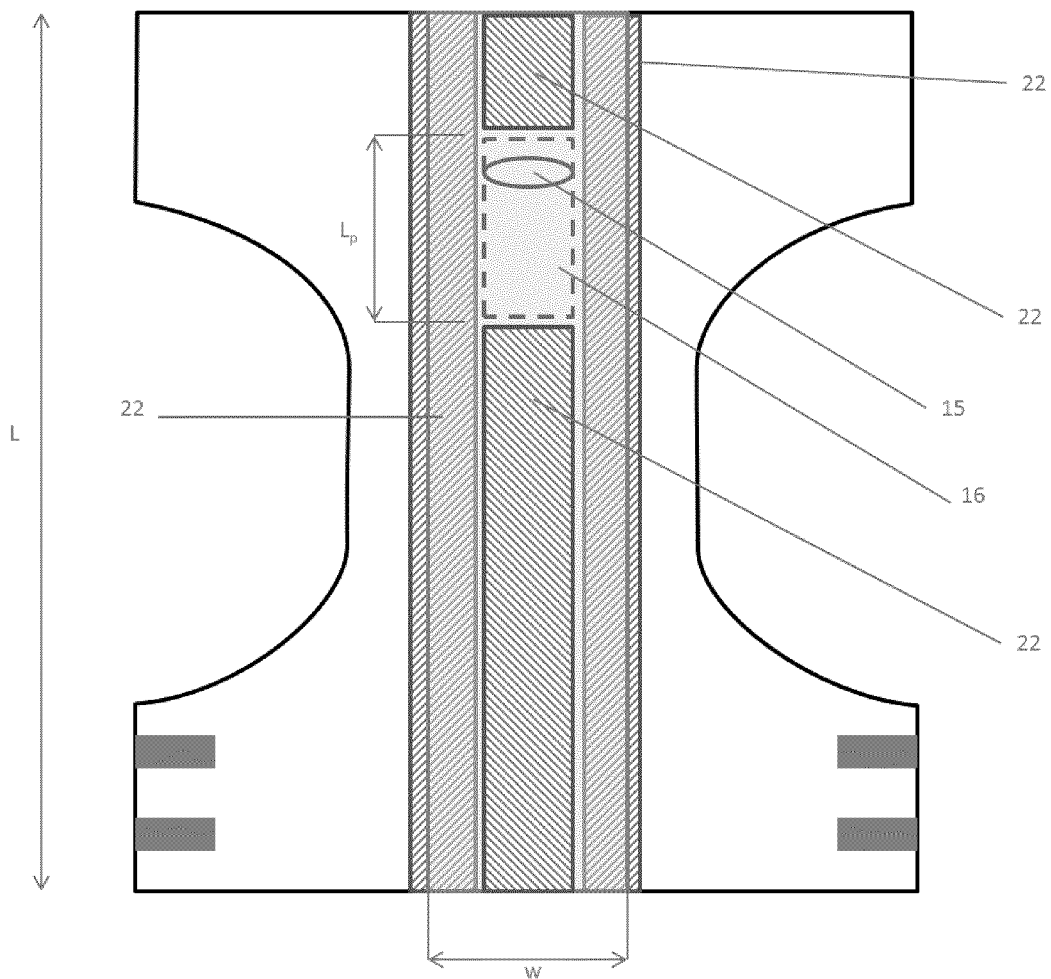
FIG. 9 is a top view schematic of a pocket and bonding arrangement according to an embodiment of the disclosure.

As exemplified in FIG. 9, the pocket 16 is preferably positioned at a distance $d_p$ from the first end 5, wherein said substrate has a length L parallel to a longitudinal axis (y-y), said distance $d_p$ being from 0L to 0.30L, preferably from 0.05L to 0.25L, preferably from 0.10L to 0.20L, more preferably from 0.12L to 0.16L. An advantage of this embodiment is to combine comfort to the wearer whilst at the same time providing good access to caregivers e.g. for abdominal injections to subjects.

Preferably the pocket 16 has a length $L_p$ of from 20 mm to 70 mm. In an embodiment, the pocket 16 has a length $L_p$ of from $0.5d_p$ to $2.0d_p$, preferably from $1.0d_p$ to $1.5d_p$, even more preferably from $1.1d_p$ to $1.4d_p$. In addition or alternatively, the pocket 16 has a length $L_p$ of greater or equal to 0.01L, preferably of from 0.02L to 0.3L, more preferably from 0.03L to 0.1L. Advantageously such sizing allows to retain a large portion of the module within the pocket and further prevent displacement thereof to allow for reliable connection of the module to the sensor tracks even upon movement of a subject in different positions, whilst at the same time providing sufficient comfort, indeed below the above-recited ranges attachment efficacy is impacted and above such ranges comfort to the user is affected as well as increase in risk of displacement of the module and false connections to the sensor tracks.

Figure 10:
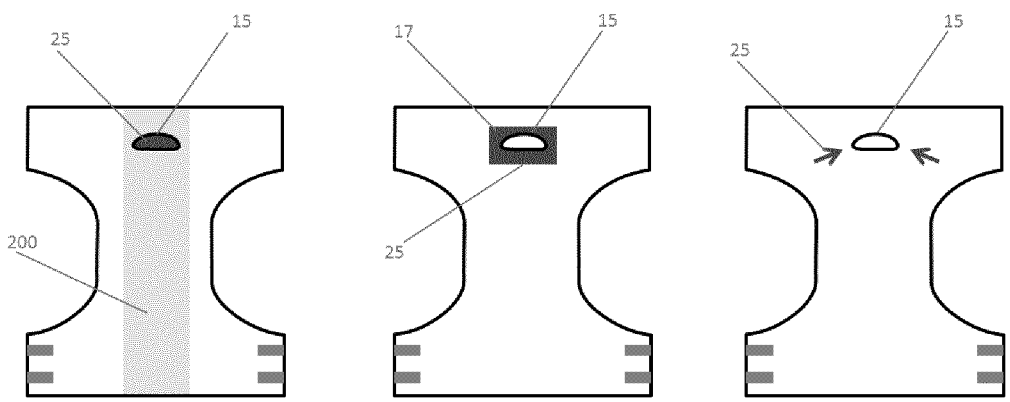
FIG. 10 is a top view schematic of alternative exemplary embodiments of guiding means for module attachment according to an embodiment of the disclosure.

As exemplified in FIG. 10, the slit(s) 15 preferably comprises one or more insertion indicators arranged to provide an indication to a user of the insertion position of the clip-on processing module 103 therethrough, preferably wherein said insertion indicator is selected from the group consisting of: indicia 25 (as used herein "indicia" meaning one or more colors or texture or printed graphics) positioned on a surface of the insulating layer 200 that faces said substrate such that said indicia is seen through said slit(s) 15; indicia, positioned on the garment facing surface of said substrate 1 such that it surrounds a perimeter of said slit(s) 15 and preferably further comprises one or more printed graphics; a patch 17 comprising indicia joinable to the garment facing surface of said substrate 1 such that it surrounds a perimeter of said slit(s) 15; and combinations thereof. Advantageously, this arrangement provides efficacious and intuitive insertion of the module at the right place to make the required electrical connection for proper operation whilst limiting excessive manipulation by the care giver.

Figure 11:
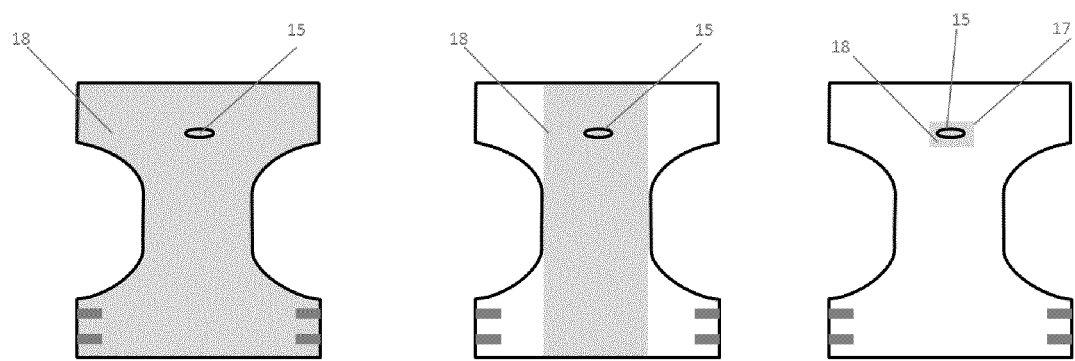
FIG. 11 is a top view schematic of alternative exemplary embodiments of reinforcement means according to an embodiment of the disclosure.

As exemplified in FIG. 11, a reinforcement layer 18 is preferably joined to a garment facing surface of said substrate 1 along a perimeter of the slit(s) 15 and at least a portion of said surface outboard of said perimeter, and wherein said slit(s) 15 forms an opening free of said reinforcement layer 18. Such arrangement advantageously reduces the risk of tear whilst manipulating the module.

In an embodiment, said reinforcement layer 18 is laminated over the entire garment facing surface of said substrate 1 except the opening; or is laminated over a central portion of said garment facing surface of said substrate 1 along a length L of said substrate 1 except said opening; or is laminated only over an area of said garment facing surface immediately adjacent to the perimeter of said slit(s) 15 except said opening.

In an embodiment, the reinforcement layer 18 is in the form of a patch, preferably said patch having a color and/or texture being visually or tactilely different from that of the garment facing surface of said substrate 1. Advantageously this allows to combine mechanical performance with visual indication for easy connection of the module.

Figure 12:
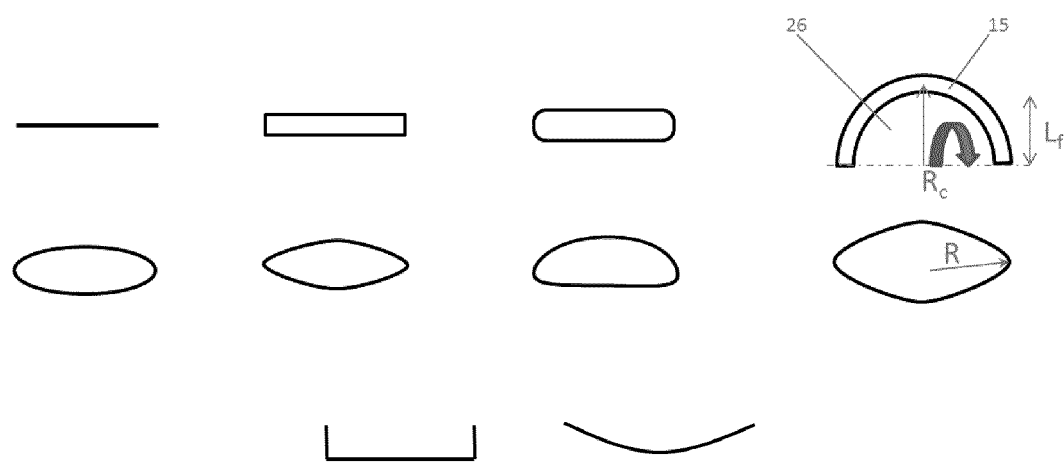
FIG. 12 illustrates schematic representations of slit geometries according to embodiments of the disclosure.

As exemplified in FIG. 12, the slit(s) 15 may be in the form of a straight linear cut, square cut, square cut with rounded edges, oval cut, rounded rhombus cut, mouth-shaped cut, and combinations thereof, preferably oval cut, rounded rhombus cut and/or mouth-shaped cut. Alternatively or in addition, the slit(s) 15 may be rounded such that a flap 26 is formed having a flap length $L_f$ arranged to be lifted with a finger for insertion of the unit 103. Preferably wherein the slit(s) 15 has a cut radius $R_c$ being greater or equal to the flap length $L_f$, more preferably wherein $L_f$ is from $0.01L_p$ to $0.5L_p$, preferably from $0.1L_p$ to $0.4L_p$.

Preferably the slit(s) 15 is free of sharp edges having a notch radius R of less than 1 mm, and preferably has a length-to-width (a/b) aspect ratio of from 1.5 to 7, preferably from 2 to 6, more preferably from 2.5 to 5, wherein said slit width extends parallel to a longitudinal axis y-y and said slit length extends perpendicular to said longitudinal axis y-y. In a preferred embodiment R is greater or equal to 3 mm, preferably greater or equal to 5 mm, even more preferably from 5.5 mm to 20 mm, even more preferably from 6 mm to 15 mm.

Without wishing to be bound by theory, the maximum stress at the tip of an ellipse (e.g. a slit/cut with rounded edges) is related to its size and shape by the following equation:

$$\sigma\max = \sigma\infty\left(1 + 2\sqrt{\frac{a}{R}}\right), \text{ and } R = \frac{b^2}{a}$$

where 2a is the length of the slit, 2b is the width of the slit and R is the notch radius (also known as radius of curvature).

Thus in order to reduce local stresses at the extremities of the slit it is desirable to shape the slit as described above to advantageously provide reduced risk of tear and crack propagation during use, such dimensions being particularly selected for the materials typically used in substrates herein such as nonwoven webs and/or polymeric films.

Figure 13:
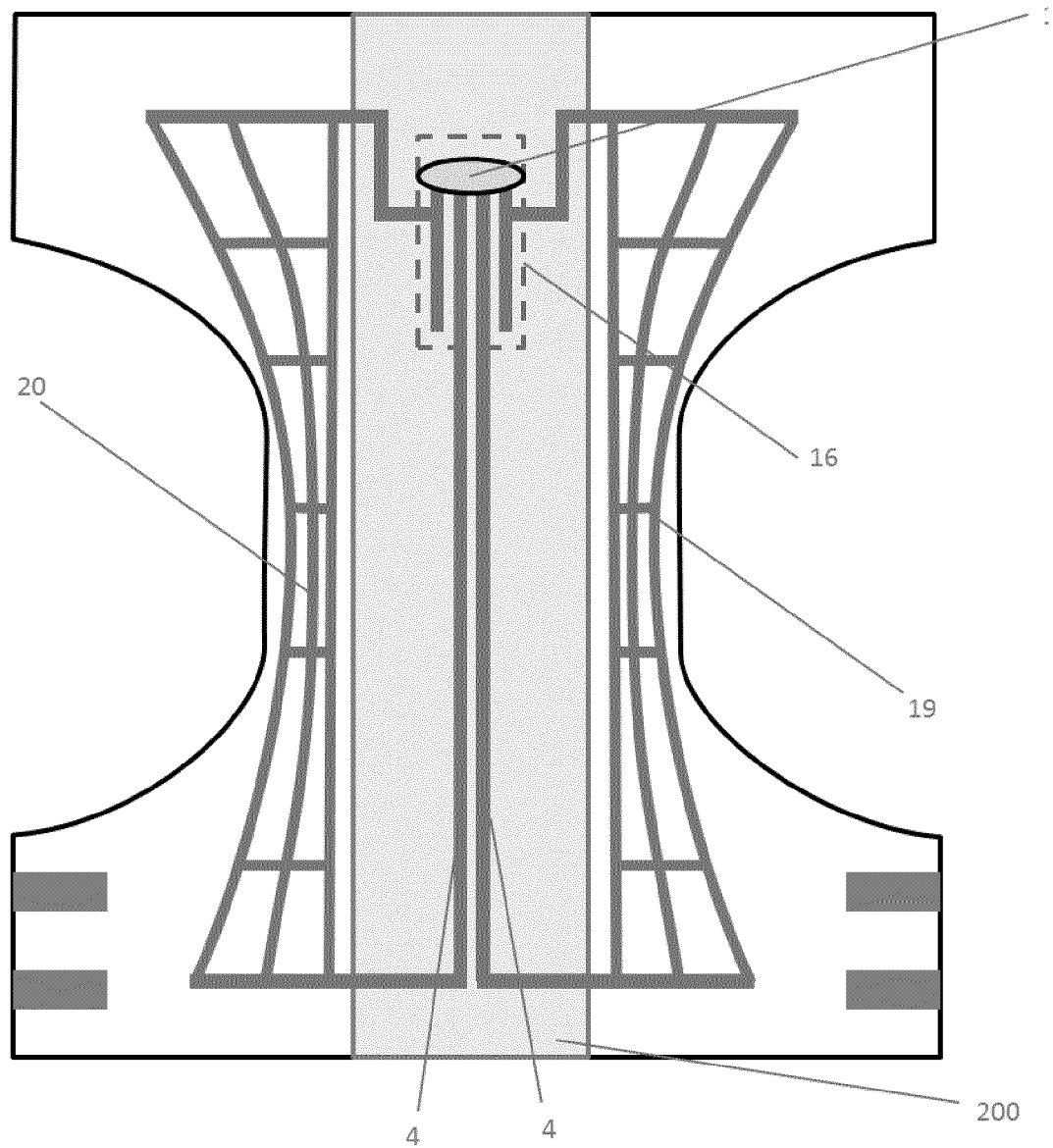
FIG. 13 illustrates a top view schematic of substrate according to an embodiment of the disclosure.

As exemplified in FIG. 13, the plurality of sensor tracks 101 are preferably divided into a right half circuit 19 and left half circuit 20 symmetrically disposed about a longitudinal axis y-y, and comprising at least two central tracks 4 extending parallel to each other along a length L of the substrate 1 each being directly connected to said right half circuit 19 or left half circuit 20 respectively, and wherein either said right half 19 is in electrical communication with said left half 20 only when the clip-on processing module 103 is connected thereto, or wherein said right half 19 and said left half 20 are not in electrical communication with each other when the clip-on processing module 103 is connected and rather remain two independent electrical circuits. Advantageously this allows for not only reduced power consumption in the wetness monitoring and thus allow for reduced battery size in the module, but further it may advantageously allow for detection of whether the leakage is happening on the left or right side of the substrate/absorbent article.

Figure 18:
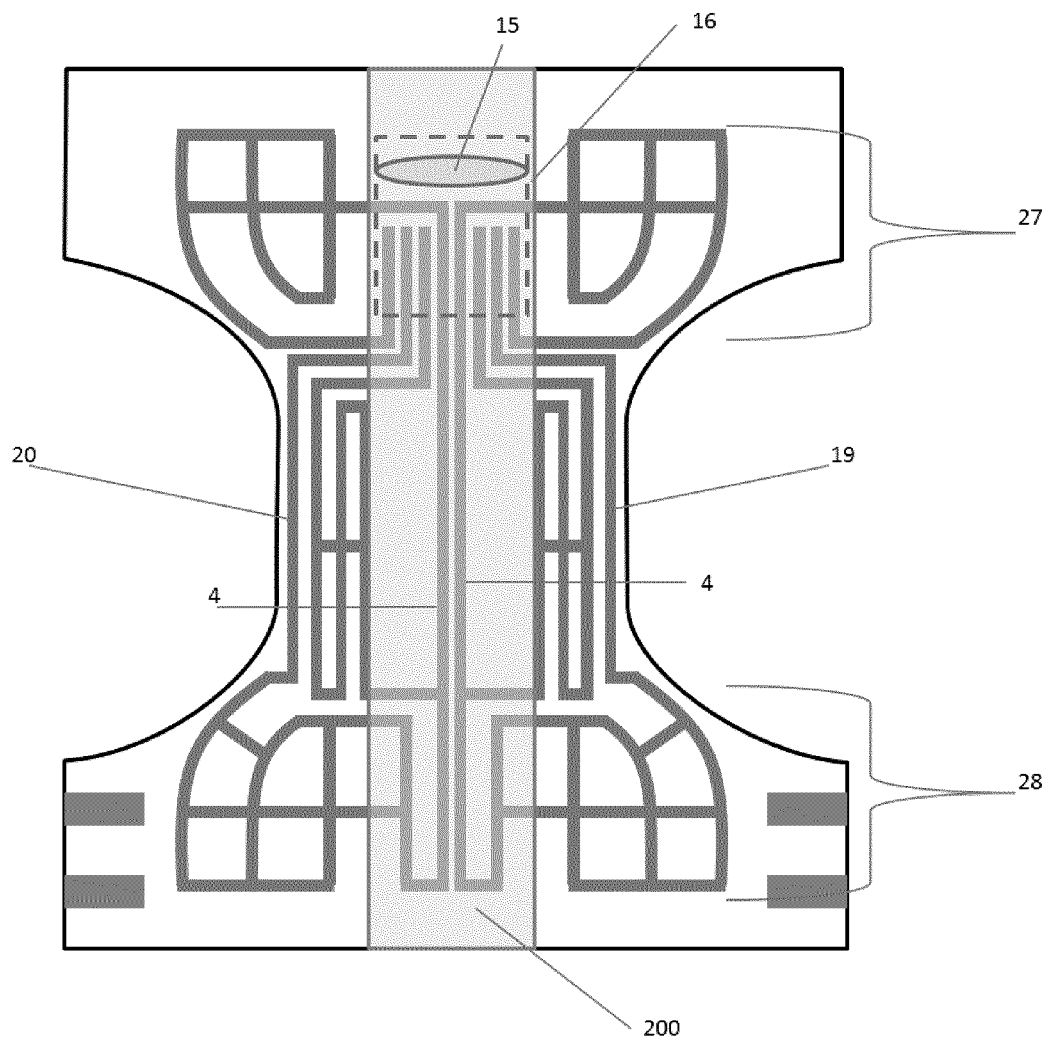
FIG. 18 illustrates a top view schematic of substrate according to an embodiment of the disclosure.

In addition or alternatively to the above described embodiment, and as exemplified in FIG. 18, the plurality of sensor tracks 101 are preferably divided into a front half circuit 27 and rear half circuit 28 symmetrically disposed about an axis perpendicular to the longitudinal axis y-y, and comprising at least two central tracks 4 extending parallel to each other along a length L of the substrate 1 each being directly connected to said front half circuit 27 and/or rear half circuit 28, and wherein either said front half 27 is in electrical communication with said rear half 28 only when the clip-on processing module 103 is connected thereto, or wherein said front half 27 and said rear half 28 are not in electrical communication with each other when the clip-on processing module 103 is connected and rather remain as two independent electrical circuits. The front half circuit 27 is preferably proximal to the pocket 16 and the rear half circuit is distal from said pocket 16. Advantageously this allows for individualized detection and determination of leakage in the front/rear ends of the substrate/absorbent article. It is herein understood that when combining this embodiment with that of the previous paragraph, the total number of sections/circuits may be four, but it is understood that more than four is also possible. As exemplified in FIG. 18, the sensor tracks 101 may comprise 3 or more arrays for each side (left/right), front/back, and crotch (or central portion of said tracks).

As explained herein above, the pocket for insertion of first part of the electrical device may be created by bonding a second strip layer on the skin facing side of the garment facing substrate. The strip layer can have the full length of the product or is just a patch at the position for creating a pocket. Bonding of the two layers may be made with hotmelt adhesives, ultrasonic bonding or other appropriate means of bonding technologies.

The pocket may have a dimension in longitudinal direction that is created by an intermittent bonding pattern that leaves open a space that matches the dimension of the first part of the device (that will be inserted). The pocket may have a dimension in cross direction that is created by the bonding pattern on each side of the strip material so that a space is left open that matches the cross directional dimension of the first part of the device (that will be inserted).

For insertion of the module, an opening cut (or slit) can be created within the garment facing layer or substrate. The opening cut can be a simple straight line or it can be a shape that requires to remove the cut out trim during the manufacturing process. The opening cut may be shaped in a way that allows to identify easily the position for insertion of the electrical device, that allows easy insertion and that can hold the device securely in place after insertion. The shape is having preferably a notch radius that creates a rounded shape with good notch toughness and good tear resistance. This may be beneficial to retain the attachment of the electrical device even when forces from the outside are working against the attachment and therefor undesirably increasing the risk of tearing the garment facing layer. The insertion of the device may be supported by the compressibility of the absorbent core underneath/behind the opening. The device can be squeezed against the garment facing layer and against the absorbent core underneath. By doing this the opening will open further and allows to slide in the device.

To reinforce the garment facing layer where the electrical device is attached a reinforcement layer can be added. The reinforcement layer increases tensile strength by combining it with the garment facing layer through a lamination process. The reinforcement layer can be either a layer entirely covering the garment facing layer or a layer covering the garment facing layer without the side panels or a layer covering the garment facing layer only with a patch at the opening position.

To help the user or the care giver to find the position for attachment of the electrical device some guidance can be provided by these construction elements. For example, either the strip layer has a colour different to the garment facing layer so that this colour can be seen through the opening or the reinforcement patch has a colour different to the garment facing layer or the garment facing layer has a print that indicates the position of the opening or a combination of said options.

The printed electrodes may be covered by the strip material against the absorbent core. The printed electrodes may be interconnected to a conductive array next to the strip material that is actually facing the absorbent core. This array being the sensor to monitor diaper intake.

In an embodiment, as shown in exemplary FIG. 1 to 4, the substrate 1, suitable for incorporation into an absorbent article 100 for automatic detection of wetness (and/or exudate) events therein, comprises a first surface 2 capable of being arranged proximal to a body facing side of the absorbent article 100 and a second surface 3 opposite said first surface 2 and capable of being arranged proximal to a garment facing side of said absorbent article 100, said substrate 1 comprising a plurality of sensor tracks 101 disposed on said first surface 2 and said sensor tracks 101 comprising: at least one central track 4 extending parallel to a length L of the substrate and parallel to a longitudinal axis y-y crossing a first end 5 and a second end 6 of the substrate 1; at least two side tracks 7,8 extending parallel to the central track 4 (by "parallel" herein it is intended substantially parallel and not necessarily limited to the side tracks extending the entire length L, although preferred) and oppositely arranged such that the central track 4 extends therebetween; and wetness sensing tracks 9 extending outboard of said two side tracks 7,8, wherein said central track 4, said side tracks 7,8, and said wetness sensing tracks 9 are in electrical communication via one or more shortening elements 10 positioned proximal to said second end 6 and distal from said first end 5, and wherein the substrate 1 is connectable to a clip-on data processing module 103 at a position proximal to said first end 5 and distal from said shortening elements 10 such to form a closed electrical circuit, typically for measuring resistance and/or capacitance therethrough. It has been advantageously found that a substrate that comprises the above described sensor track arrangement provides for accurate detection of exudates as well as being particularly suitable for fully scalable in-line mass production at high speeds, without the need to change arrangement depending on product sizes. For example, an advantage of positioning the wetness sensing tracks outboard of the other tracks is that if/when the substrate is cut to form for example leg openings (which may vary depending on product size), the circuitry is not damaged (since e.g. the central feedback track would always remain intact) and wetness detection is still ensured across the areas of greater risk of leakage that are located proximal to the edges and/or sides of the absorbent article.

Preferably, the central track(s) 4 has the highest conductivity compared to other sensor tracks 101.

In an embodiment, the distance between the at least two side tracks 7,8 is less than 0.3W, wherein W is the width of the substrate 1 extending perpendicular to the length L thereof. Preferably, said distance is less than 0.2W, more preferably said distance is from 0.01W to 0.18W, even more preferably from 0.04W to 0.15W. Advantageously, limiting the distance between said tracks allows for a larger wetness sensing surface area for wetness event detection and may further make any subsequent insulation of the feedback track easier to achieve in fast inline production as will be further explained in the following embodiments.

In an embodiment, the distance between each side track 7,8 and lateral side edges 12,13 of the substrate 1 is greater than 0.2W, preferably greater than 0.25W, even more preferably from greater than 0.26W to less than 0.5W, even more preferably from 0.27W to 0.47W, most preferably from 0.3W to 0.4W. Similarly to the above, it is not only desirable that the side tracks are spaced close to each other but further that the distance between each side track and the lateral edges of the substrate is as high as possible in order to increase the sensing area covered by the wetness sensing tracks 9.

In an embodiment, the central track 4 extends along a centerline of the substrate 1 running along the longitudinal axis y-y. Preferably wherein each side track 7,8 is symmetrically disposed on either side of said central track 4. An advantage of this arrangement is that shorting distances are reduced hence limiting the risk of circuit failure and/or signal noise.

In a preferred embodiment, the substrate 1 consists of a liquid impermeable backsheet 141, preferably a breathable liquid impermeable backsheet 141.

In an embodiment, the wetness sensing tracks 9 are characterized by resistance (or more generally speaking impedance) values. Indeed, resistive measurements described herein are not limited to direct current (DC) power sources but also and most preferably alternating current (AC) power sources. Said wetness sensing tracks 9 generally having an adjusted resistance/impedance design, that can further be defined by a mathematical distribution model in the variation of respective resistance/impedance values over a surface of the absorbent article, said distribution model may be a linear, quadratic or logarithmic, preferably logarithmic, distribution.

In a preferred embodiment, the resistance/impedance of the wetness sensing tracks 9 proximal to the lateral side edges 12,13 and/or first/second ends 5,6 of the substrate 1 is greater than on any other portion of said substrate 1 (typically said other portions being inboard of said lateral side edges 12,13 and/or first/second ends 5,6 and proximal to the middle and/or center of the substrate 1). In an alternative embodiment said resistance/impedance is substantially the same throughout the wetness sensing tracks 9.

Especially, but not only, in the latter embodiment (i.e. also independently therefrom) the wetness sensing tracks 9 may form a grid pattern across the substrate 1 wherein said grid comprises resistive (and/or conductive) elements running both substantially parallel to the longitudinal axis y-y as well as substantially perpendicular thereto. The latter arrangement is beneficial for ensuring reliable sensing of wetness events also upon saturation of the product which inevitably results in expansion of the absorbent core 143 of the absorbent article and thus more prone to delamination of the absorbent core components (e.g. the core wrap) from the backsheet 141. Surprisingly such a grid structure has been found to be beneficial in providing continued and reliable detection also in such extreme conditions.

In a preferred embodiment, the grid pattern may vary across the surface of the substrate 1, and arranged such that the distance between each resistive (and/or conductive) elements (also referred to herein as members) is lower at positions proximal to the lateral edges 12,13 and the sides 5,6 of the substrate 1 as compared to other regions of the substrate 1 typically proximal to the center thereof. An advantage is to permit accurate risk of leakage detection which has been found most necessary at proximity to the edges of the product.

In an embodiment, the resistance/impedance of the wetness sensing tracks 9 varies cross the surface of the substrate 1, preferably such that it is higher in regions proximal to the lateral side edges 12,13 of the substrate 1. The resistance/impedance may be increased by limiting the amount of electrically conducting/conductive material, for example in the instance of printed sensor tracks, the tracks may be made thinner and/or the total % wt of printed sensor tracks proximal to said lateral side edges may be lower than the total % wt of printed sensor tracks distal from said lateral side edges 12,13 and proximal to a center of the substrate 1.

Preferably, the sensor tracks 101 comprise an electrically conductive material, and are preferably printed sensor tracks. In a preferred embodiment, the printed sensor tracks 101 comprise, preferably consist of, a carbon-based ink and/or a conductive polymer-based ink, preferably the carbon-based ink comprising a conductive compound selected from the group consisting of graphene, graphite, nano-carbon-tubes and mixtures thereof, preferably the conductive polymer-based ink comprising a conductive compound selected from the group consisting of polyacetylene, polypyrrole, polyaniline and copolymers thereof, more preferably selected from the group consisting of poly(pyrrole)s (PPY), polyanilines (PANI), poly(thiophene)s (PT), poly(p-phenylene sulfide) (PPS), poly(p-phenylene) (PPP), Poly (acetylene)s (PAC), Poly(p-phenylene vinylene) (PPV), poly(3,4-ethylenedioxythiophene) (PEDOT), and mixtures thereof, most preferred conductive polymer-based ink comprising poly(3,4-ethylenedioxythiophene) polystyrene sulfonate (PEDOT:PSS). An advantage of this arrangement is that fast production is achieved whilst ensuring good compatibility with the end/final product unlike with the addition of foreign conductive elements like copper wires and the like, which are more prone to tearing the liquid impermeable substrate. Indeed, it is preferred in the disclosure herein to avoid metal containing inks (i.e. ink is free of metals) particularly due to the environmental impact to disposability.

In a highly preferred embodiment, the substrate 1 further comprising an insulating layer 200, preferably being liquid impermeable, adhered thereto and sized to cover the at least one central track 4 and at least a portion of the side tracks 7,8 (typically said "at least portion" being proximal to a position where the clip-on data processing module is connected to said substrate), said insulating layer 200 adapted to provide a seal and/or barrier to liquid from coming into contact with said central track 4 and said at least portion of side tracks 7,8, preferably wherein the wetness sensing tracks 9 remain exposed and are not covered by said insulating layer 200. An advantage of this arrangement is that the insulating layer protects the central tracks and portions of the side tracks from coming into direct contact with exudates and thus limiting the risk of false positives, noise and even failure of detection. This not only along the length L for the central track but importantly also the side tracks for portions proximal to the connection position of the clip-on unit.

In an embodiment, the insulating layer 200 is a nonconductive substrate such as a film typically comprising polyethylene, alternatively the insulating layer 200 is in the form of a non-conductive adhesive (preferably a hotmelt adhesive) and/or non-conductive ink. In case the shortening elements are printed on the insulating layer it may be desirable to use conductive adhesive to connect the printed tracks of the substrate to the printed shortening elements of the insulating layer conductively together. The use of conductive adhesive may be limited to certain spots where the conductive connection is interdentally created while in other positions it may be desirable to avoid a shortening between central track and side track through the conductive adhesive.

In an embodiment, the insulating layer 200 has a length extending parallel to the length L of the substrate 1 that is equal or less than said length L of the substrate 1. Preferably the length of said insulating layer 200 is from 0.8L to L, preferably from 0.85L to 0.99L.

In a highly preferred embodiment the width w of the insulating layer 200 is less than the width W of the backsheet 141 (and/or substrate 1), preferably is less than 0.5W, more preferably from 0.05W to 0.35W, even more preferably from 0.08W to 0.30W, most preferably from 0.1W to 0.2W.

In a preferred embodiment, the insulating layer 200 has a thickness (typically extending along an axis perpendicular to both the length and width w of said insulating layer) of 0.7 mm or less, preferably from 0.005 mm to 0.500 mm, more preferably from 0.010 mm to 0.200 mm, more preferably from 0.015 mm to 0.08 mm. Thickness measurements may be made according to ASTM D1777 and typically using a thickness tester such as C640, or CHY-C2A of Labthink International, 200 River's Edge Drive, Medford, MA, USA.

Preferably, the insulating layer 200 comprises the one or more shortening elements 10, such that the central track 4, the side tracks 7,8, and the wetness sensing tracks 9 are in electrical communication via said shortening elements 10 when said insulating layer 200 is joined to the substrate 1. An advantage of this arrangement is that it allows a non-registered process to be used in processing the substrate, indeed registered printing of backsheets would add complexity and cost to the overall production.

In an embodiment, the substrate 1 comprises at least two, preferably at least three, central tracks 4 extending parallel to each other, and further being in electrical communication with each other via one or more secondary shortening elements 11, preferably said secondary shortening elements 11 being located distal from the shortening elements 10 and between said shortening elements 10 and the first end 5 of the substrate 1 typically such to provide one or more resistance identifiers, most preferably wherein the insulating layer 200 comprises said secondary shortening elements 11. An advantage is that identifiers such as the level of absorbency of the absorbent article, the size etc. can be pre-defined and detected when connected to the clip-on module, based on the location of the secondary shorts generating a pre-set resistance level that the module can detect by comparing for example the initial resistive measurement upon connection to the absorbent article versus preset values that may be stored in a memory within the unit.

Figure 7:
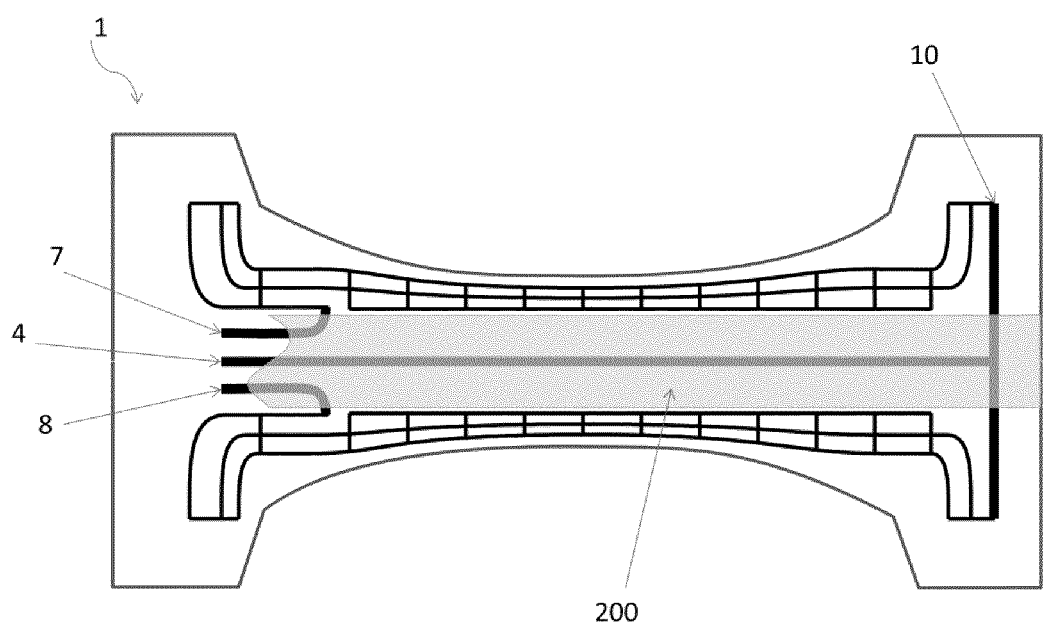
FIG. 7 is a top view schematic of a substrate according to an embodiment of the disclosure.
Figure 8:
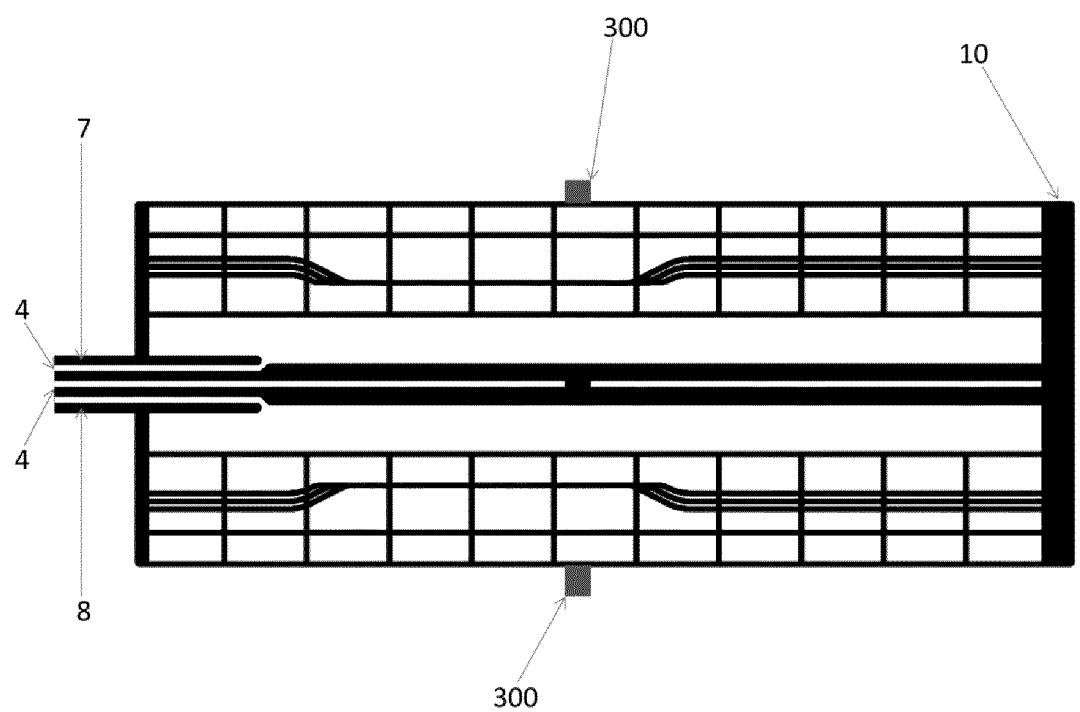
FIG. 8 illustrates an exemplary embodiment of a print pattern suitable for an embodiment of the present disclosure.

In an alternative embodiment, as shown in FIGS. 7 and 8, when the sensor design is generally registered, the shortening elements 10 and/or secondary shortening elements described herein are directly comprised on the substrate 1 and not on the insulating layer 200. In such embodiments the wetness sensing tracks 9 may comprise more than one densified areas wherein said densified areas are formed by a higher concentration of said sensing tracks 9 compared to other areas of said sensing tracks 9 (e.g. reduced pitch between elements of the sensing tracks 9 versus the pitch between elements of said sensing tracks 9 in the other areas, or a higher surface area coverage of said sensing tracks 9 versus the surface area coverage in the other areas). Preferably, said densified areas are located at a position proximal to the lateral side edges 12,13 at a central portion of the crotch region and/or at positions proximal to the contour of an absorbent core 143 when laminated over the substrate to form the assembled absorbent article. As shown in FIG. 8, the sensor design my comprise registration marks 300 arranged to provide a trigger to a registering device to carry out process steps, such as cutting, at a precise position during the manufacturing process and assembly of the substrate to other components for assembling the final absorbent article.

When the substrate 1 comprises two or more central tracks 4, the longitudinal axis y-y may extend in between at least two of said two or more central tracks 4. An advantage of this arrangement is that it enables reliable location of the clip on module for correct and appropriate electrical connection to the respective tracks.

In an embodiment, at least a substantial portion of the wetness sensing tracks 9 remains exposed to liquids and are not covered by the insulating layer 200. Preferably at least 90%, more preferably at least 95%, even more preferably at least 98%, most preferably 100%, of the surface area of the wetness sensing tracks remains exposed.

In an embodiment, the wetness sensing tracks 9 are in the form of a repeating grid and/or pattern along the length L of the substrate 1 and a dimension substantially perpendicular thereto, said grid and/or pattern preferably comprising a plurality of at least partially interconnected resistive members 301, 302, 303, 304, 305, 306 each having a shape selected from straight lines; curved lines; wave-like; geometrically shaped such as squares, parallelogram, triangles, circles, ellipses, dots, and combinations thereof; decorative elements such as flowers, butterflies, and combinations thereof; and combinations thereof. Preferably, the wetness sensing tracks 9 form of a repeating grid or pattern along the length L of the substrate 1 and a dimension perpendicular thereto, said grid and/or pattern preferably comprising a plurality of at least partially interconnected resistive members each having a shape selected from straight lines and/or curved lines, where lines can be replaced by interconnected decorative elements that form a pattern along the track. The width of said lines and/or the connected pattern that is replacing the lines may be of up to 50% of the distance between neighboring tracks. The tracks in longitudinal direction may be arranged in parallel to the side tracks 7,8 or at an angle to it of up to 45°, preferably from 2° to 30°, more preferably from 5° to 25°. Other tracks can be arranged perpendicular to the side tracks 7,8 or on an angle to it of up to +/−45° preferably from 2° to 30°, more preferably from 5° to 25° (the angles measure either as a positive or negative angle e.g. +45° or −45°).

In a preferred embodiment, a plurality of the resistive members, preferably a majority, more preferably all, extending in a direction towards the lateral side edges 12,13 of the substrate 1 are at an angle α to the longitudinal axis y-y, said angle α being from 2° to 45°, preferably from 5° to 30°, more preferably from 8° to 25°, even more preferably from 10° to 20°. An advantage of this arrangement is that during the application step in the process, a reduction of the wear and tear of the components is achieved compared to when the members extend at angles of greater than 45° (especially right angles). This arrangement has been found beneficial to still provide accurate sensing also at saturation conditions (which may lead to delamination issues as described above) hence making it a highly optimal arrangement from both a functionality as well as production point of view.

Preferably, a plurality of the resistive members wetness sensing tracks 9, preferably a majority, more preferably all, extending in a direction towards the first and/or second ends 5,6 of the substrate 1 are at an angle β to the longitudinal axis y-y, said angle β being from 2° to 45°, preferably from 5° to 30°, more preferably from 8° to 25°, even more preferably from 10° to 20°. An advantage of this arrangements is that the benefits described above are further exacerbated.

Figure 3:
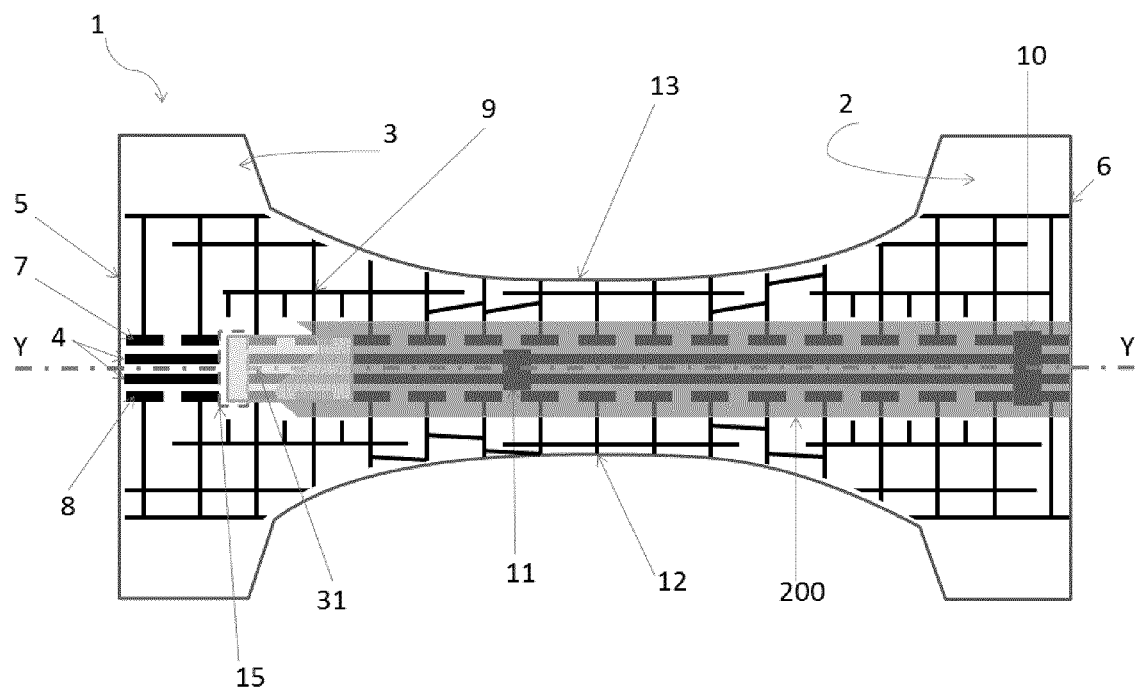
FIG. 3 illustrates a top view schematic of substrate according to an embodiment of the disclosure.
Figure 4A:
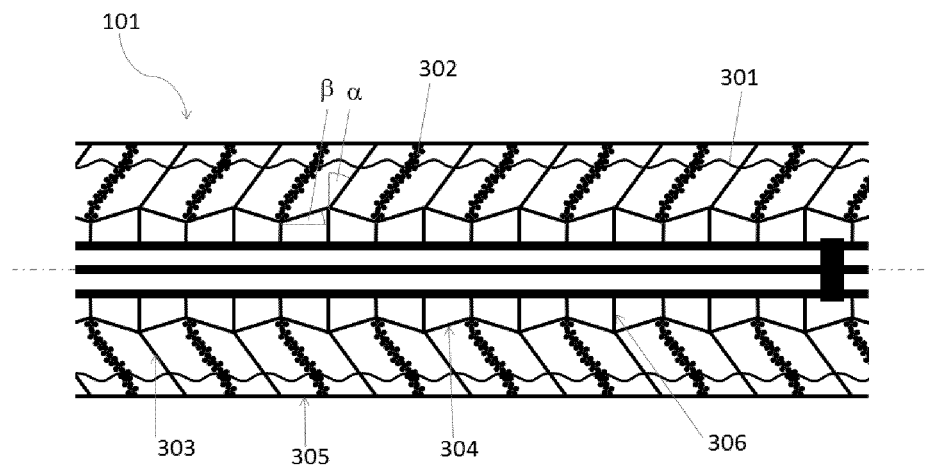
FIG. 4A-B illustrate embodiments of portions of the sensor tracks according to the present disclosure.
Figure 4B:
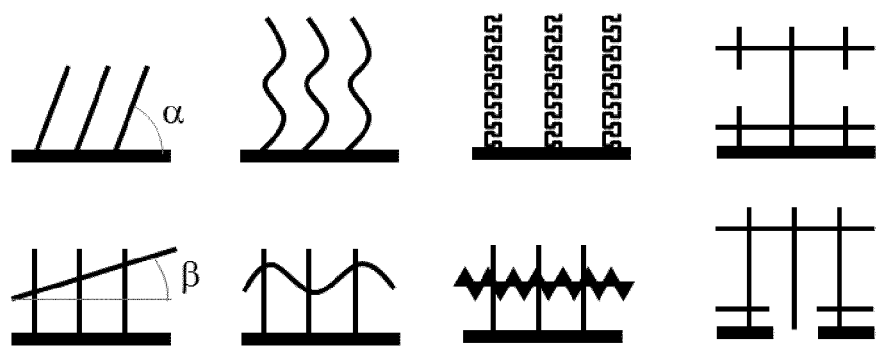

In an embodiment as shown in exemplary FIG. 3, at least one, preferably each, of the side tracks 7,8 is discontinuous along an axis parallel to the length L of the substrate 1 such to force a current through the wetness sensing tracks 9 towards regions proximal to lateral edges 12,13 of the substrate 1 said lateral edges 12,13 extending between the first and second ends 5,6 and along the length L of the substrate 1, preferably wherein at least a portion of the wetness sensing tracks 9 are further alternatingly directly connected and disconnected to the respective side tracks 7,8 along the length L of the substrate 1. Preferably said portion of the wetness sensing tracks 9 is proximal to the first and/or second ends 5,6 of the substrate 1. An advantage of this arrangement is that better accuracy of exudate detection is achieved where it is needed most for assessing risk of leakage i.e. proximal to the sides and/or ends of the substrate. Moreover, by having an alternating connection of the wetness sensing tracks as shown in FIG. 3 in regions proximal to the first and/or second ends, improved detection capability is enhanced also proximal to the central portion of the substrate in regions where further potential leakage and/or discomfort may occur. Such arrangement has surprisingly been found beneficial when using a random non-registered print design.

In an embodiment, the wetness sensing tracks 9 are non-evenly distributed across the surface of the substrate 1 and arranged such that portions of said wetness sensing tracks proximal to the lateral edges 12,13 of the substrate 1 are thinner than those portions distal therefrom and proximal to the center of the substrate. Preferably, tracks running perpendicular to the longitudinal axis y-y are thinner than those running parallel thereto.

In any of the embodiments herein, the substrate 1 further comprises temperature sensing tracks outboard of the wetness sensing tracks. An advantage of this embodiment is that by further monitoring temperature at the extremities of the substrate a more accurate detection of leakage may be gathered in addition to the resistance/capacitance measurements.

The Absorbent Article

Figure 5:
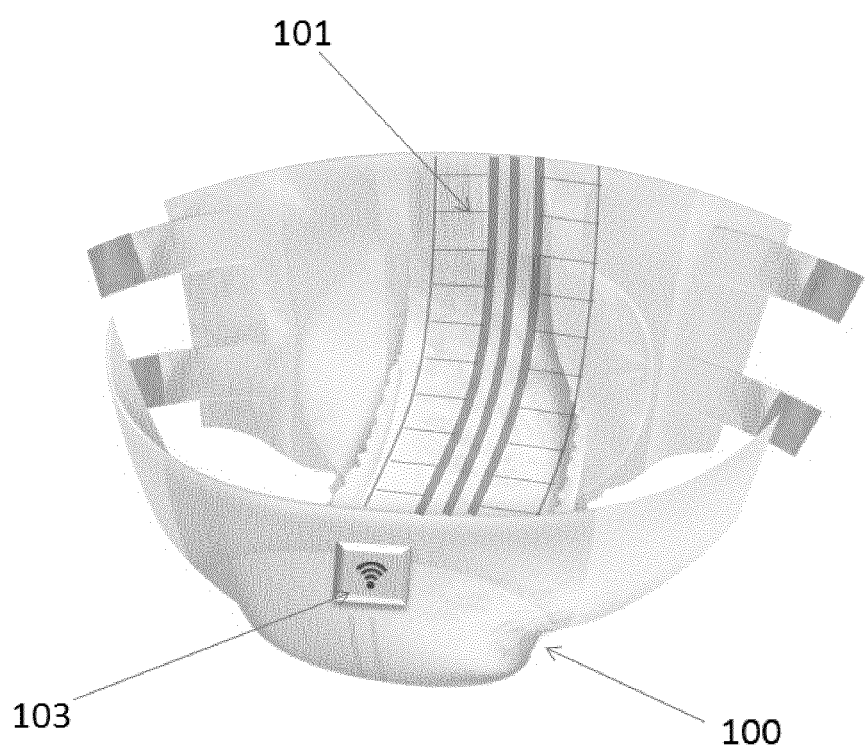
FIG. 5 is an isometric schematic view of an absorbent article according to an aspect of the present disclosure.

In an embodiment, the absorbent article 100 according to the present disclosure (as exemplified in FIG. 5) is typically a disposable diaper, pad or pant, and suitable for detecting a wetness (i.e. urine and/or feces) event therein and/or risk of exudate leakage therefrom, said absorbent article comprising: a liquid impermeable backsheet 141; a liquid permeable topsheet 142; and an absorbent core 143 interposed between said backsheet 141 and topsheet 142, wherein said backsheet 141 comprises the substrate 1 described herein, typically the backsheet 141, absorbent core 143 and topsheet 142 forming a chassis of the absorbent article.

Figure 14:
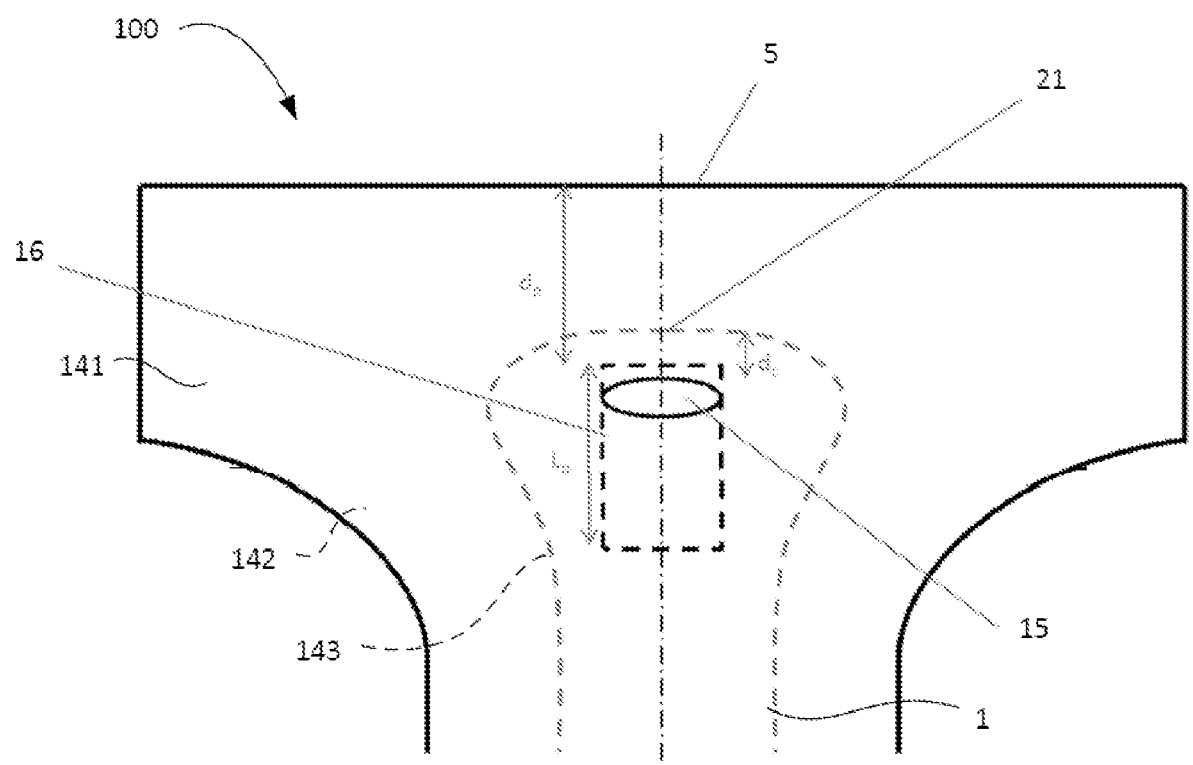
FIG. 14 is a partial top view schematic illustrating the pocket positioning relative to the core, according to an embodiment of the disclosure.

As exemplified in FIG. 14, the pocket 16 may be positioned within a core region, and preferably at a distance $d_c$ from a core proximal edge 21, said pocket 16 having a pocket length $L_p$, and wherein $d_c$ is from $0.01L_p$ to $0.3L_p$, preferably from $0.05L_p$ to $0.25L_p$, more preferably from $0.08L_p$ to $0.20L_p$. Advantageously such arrangement allows for good comfort and cushioning provided by the core layer through its thickness. By "within a core region" it is meant that the pocket is positioned such that a portion of the core 143 is interposed between the subject and said pocket (and e.g. module when inserted/connected thereto) when the article is being worn.

Figure 15:
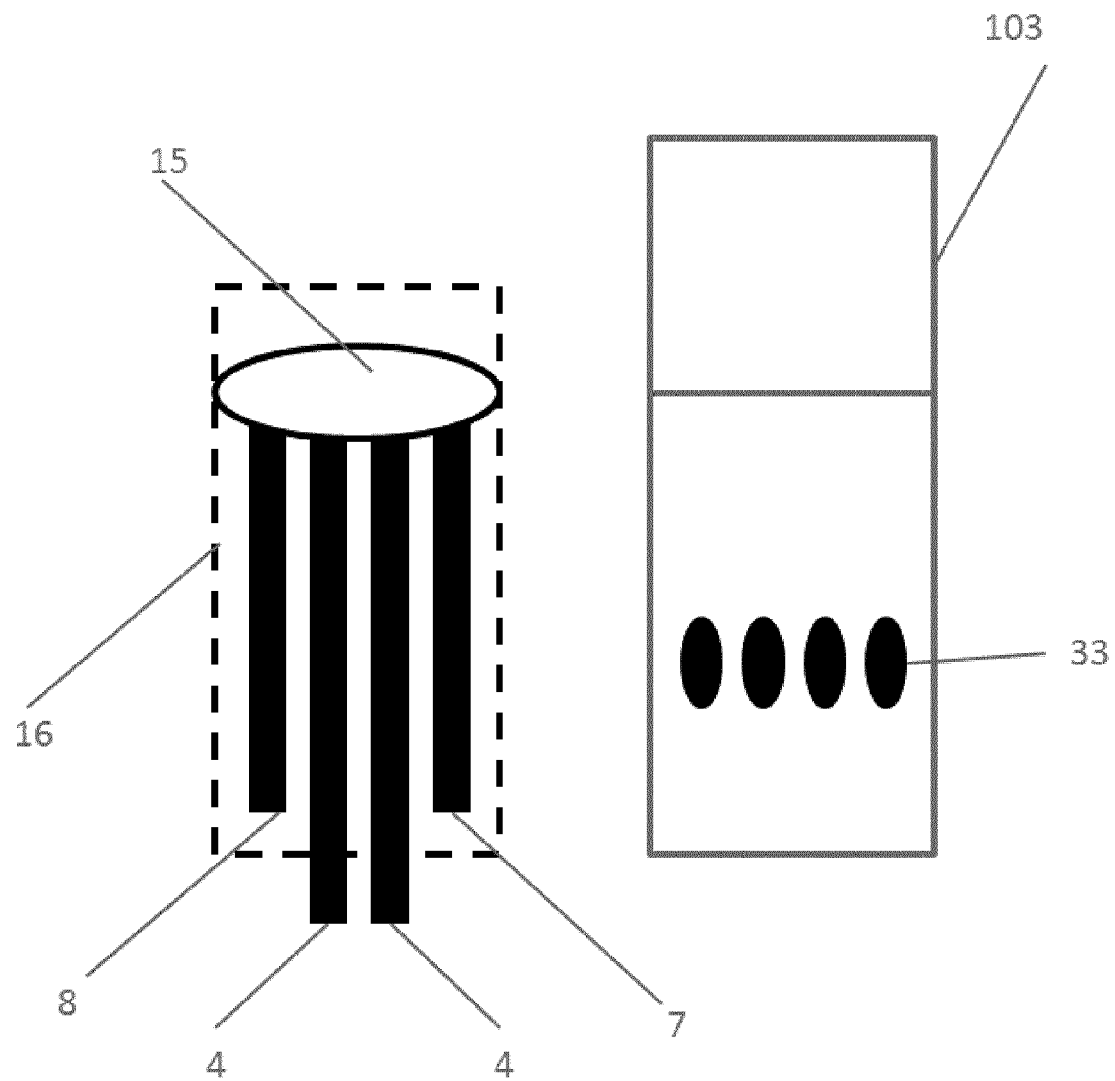
FIG. 15 is a schematic illustrating a pocket and module according to an embodiment of the disclosure.

Preferably, as exemplified in FIG. 15, the article further comprising a removable clip-on data processing module 103 having a plurality of exposed electrically conductive terminals 33 capable of directly contacting central 4 and side 7,8 tracks of the plurality of sensor tracks 101, preferably wherein the number of said terminals 33 is at least the same as the number of said central and side tracks 4,7,8. For example, the terminals may be sized in sufficient length to ensure appropriate connection with the sensor tracks or may comprise a multiple of said terminals arranged in series to ensure optimal connection.

Figure 16:
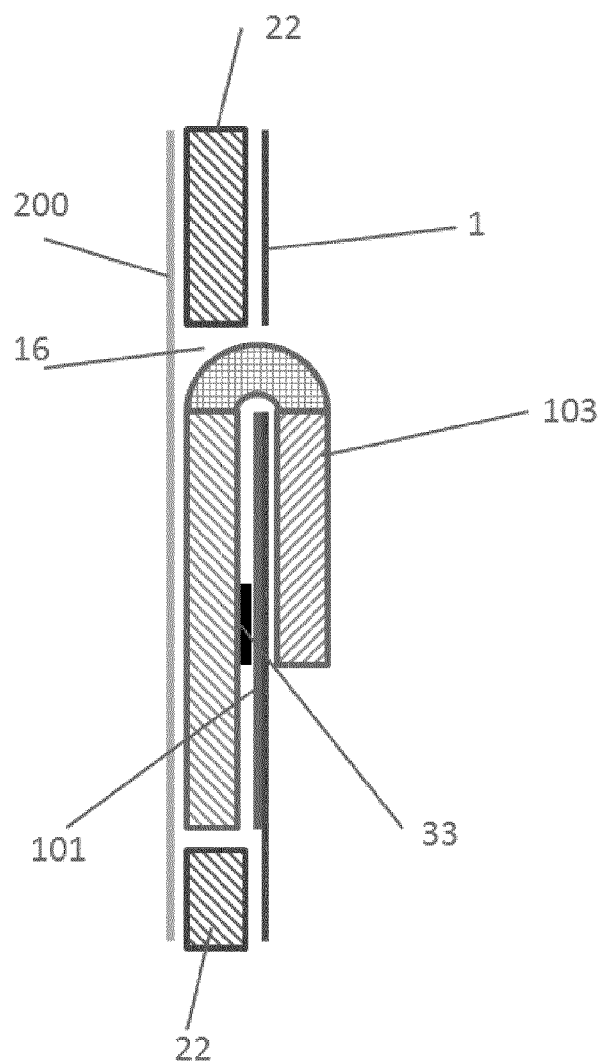
FIG. 16 is a cross-section schematic of a module being inserted into the pocket according to an embodiment of the disclosure.

Preferably, as exemplified in FIG. 9 and FIG. 16, at least a portion of the clip-on data processing module 103 is retainable or retained within the pocket 16, said pocket being delimited along its perimeter by a bonding seal 22, preferably selected from an adhesive material, and along its garment facing outer surface by the garment facing surface of the substrate 1 and along its skin facing (also referred to as body-facing) inner surface by the insulating layer 200, typically wherein said portion is the one comprising the exposed electrically conductive terminals 33.

Figure 17:
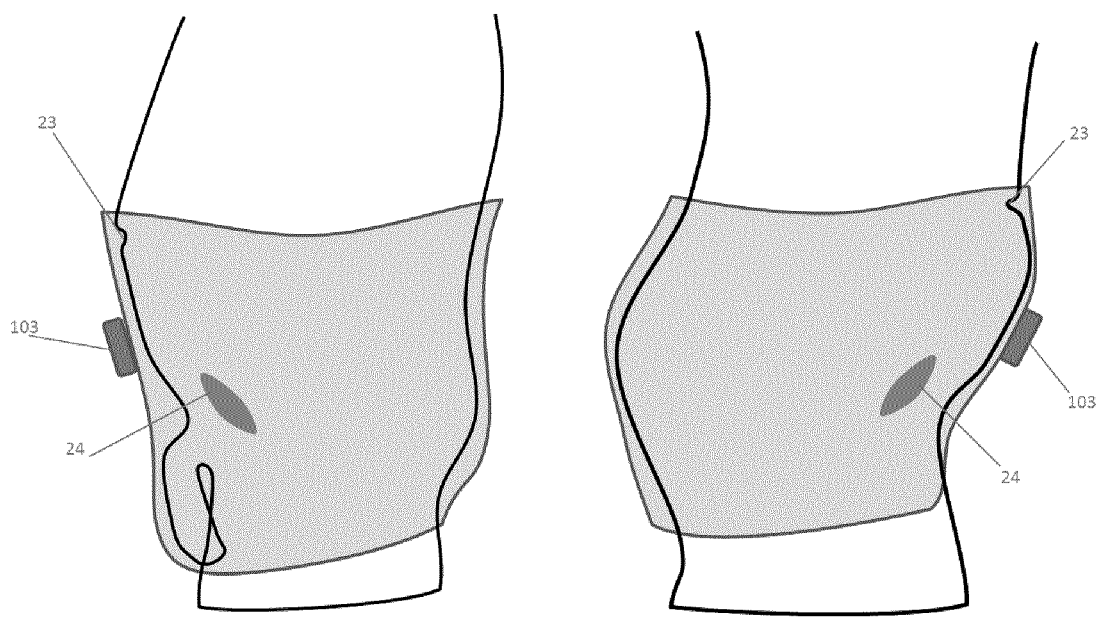
FIG. 17 is schematic side view of a male and female subject wearing an absorbent article according to an embodiment of the disclosure.

As shown in FIG. 17, the position for the pocket (i.e. position of module attachment) is preferably chosen to ensure good wearing comfort and good accessibility for care givers. The placement is preferably at the front side of the wearer, below the belly button position 23, so that medical injections to the patient at this point are not hindered. The placement is also not too low and preferably above the pubic bone position 24 to ensure good wearing comfort. The point of attachment is preferably at a position that provides some cushioning and buffering with the absorbent core 143 underneath.

In an embodiment, the absorbent article 100 is arranged to measure and monitor the amount of exudates across a surface covered by the wetness sensing tracks 9, combined with detection of the position of the subject (e.g. sitting, lying on back or side etc.) by the motion sensor comprised in the module 103 described herein above. The position information may then be used by the processor to calculate an effect of said position (e.g. angled gravity effects) on the speed of saturation at a given area of the absorbent article and is compared and/or combined with sensed wetness signals received in said given area by the respective portion of the wetness sensing tracks 9. Preferably, the saturation level is determined for a plurality of individual and/or local areas within the absorbent article. This is advantageous over prior art systems that rather provide total saturation information, in that leakage risk may actually be high in a specific single region of the absorbent article even if the overall/total saturation of the absorbent article is far from being reached. In such instances, leakage may still occur and a warning to the care giver not provided, to the contrary the absorbent articles described herein advantageously monitor area-specific wetness information combined with position data in order to more effectively warn care givers when the risk of leakage is high such to prompt an intervention (e.g. rotate the patient to a new position or replace the absorbent article).

Not only the volume inside an absorbent article defines the moment of leakage, but the position of a person's body over time also plays a fundamental role in determining the distribution of the liquid inside the absorbent article. The present disclosure addresses this with the combination of totally absorbed volume and more accurate position detection of a person's body (e.g. lying (on the belly/back/left side/right side), sitting or standing) over time determines when an absorbent article will most likely start leaking. The more accurate position detection as referred to, is for instance not only related to lying or sitting, but implying that a person is lying on a particular side of its body, or in case of sitting, that a person is sitting straight or under a certain angle. It has surprisingly been found that the particular sensor track arrangement described herein synergistically operates with the position sensing system to provide accurate determination of risk of leakage in use.

The absorbent article may further comprise additional components that are common in the art and selected from the group consisting of: a liquid distribution layer (ADL) positioned between the topsheet 142 and the absorbent core 143; elastic or non-elastic back ears joined to the chassis at a position proximal to the second end 6 of the substrate 1 forming the backsheet 141; super absorbent polymer particles and/or fibers typically comprised within the absorbent core 143; cellulose fibers typically comprised within the absorbent core 143; fastening tapes joined to the back ears for adhesive and/or mechanical coupling with a garment facing surface of the backsheet 141 at a position proximal to the first end 5; elastic waistband positioned proximal to the first and/or second ends 5,6; and combinations thereof. When the absorbent article is a pant, the absorbent article may comprise a front belt positioned proximal to the first end 5 and a rear belt positioned proximal to the second end 6, said belts being separated from each other by the chassis of the absorbent article and being directly joined to each other via two opposite side seams, said belts typically being elastic. When the absorbent article is a pad it may be designed as a two-piece system, where the second piece is an elastic pant (reusable or disposable) to hold the first piece—said absorbent article—securely in place.

In an embodiment, the absorbent core 143 comprises a nonwoven core wrap typically arranged such that there is no folding (i.e. no nonwoven overlap) of said core wrap coming in direct contact with the backsheet 141 comprising the sensor tracks. The nonwoven core wrap has typically hydrophilic properties, so that is allows the liquid to get in contact to the wetness sensing tracks.

In an embodiment, the absorbent article comprises a removable clip-on data processing module 103 adapted to monitor and process resistance and/or capacitance data acquired from the wetness sensing tracks 9, said clip-on data processing module 103 being connectable to the at least one central track 4 and the at least two side tracks 7,8 via a slit 15 and/or pocket on the backsheet 141 enabling an electrically conductive portion of said module 103 to directly come in electrical communication with said at least one central track 4 and said at least two side tracks 7,8, preferably the slit and/or pocket arranged to accommodate at least 50%, preferably at least 60%, more preferably at least 70%, even more preferably at least 80%, of the total surface area of the clip-on data processing module 103 therein. An advantage of this arrangement is that the module remains nicely secured to the absorbent article as well as being protected from accidental disengagement during movements of the subject/wearer.

Preferably, the substrate 1 is positioned such that the first surface 2 faces the absorbent core 143, and preferably wherein the insulating layer 200 is joined to said substrate 1 such that a liquid impermeable seal is formed providing a barrier to exudates expelled by a subject, when wearing the absorbent article, from coming into direct contact with the at least one central track 4 and at least a portion of the at least two side tracks 7,8. Preferably, said insulating layer 200 is adapted to prevent liquid from coming into contact with said central track 4 and at least a portion of said side tracks 7,8. It is highly preferred that at least a substantial portion of the wetness sensing tracks 9 remains exposed and not covered by said insulating layer 200.

In an embodiment, the insulating layer 200 comprises the one or more shortening elements 10, such that the central track 4, the side tracks 7,8, and the wetness sensing tracks 9 are in electrical communication via said shortening elements 10 only when said insulating layer 200 is joined to the substrate 1. An advantage of this arrangement is that a greater degree of flexibility is provided as well as simplifying the process of assembly for reasons that will be better explained in the process section herein and thus allowing for an effective non-registered process to be used.

In an embodiment, the insulating layer 200 adheres to the backsheet 141 via a non-electrically-conductive adhesive and/or mechanical bonding, wherein the mechanical bonding is preferably selected from ultrasonic bonding, thermal bonding, and combinations thereof. An advantage of this arrangement is that noise and/or risk of compromising the wetness detection data is minimized. In case the shortening elements are printed on the insulating layer it may be desirable to use conductive adhesive to connect the printed tracks of the substrate to the printed shortening elements of the insulating layer conductively together. The use of conductive adhesive may be limited to certain spots where the conductive connection is interdentally created while in other positions it may be desirable to avoid a shortening between central track and side track through the conductive adhesive.

In a preferred embodiment, the adhesive and/or mechanical bonding is comprised across a length and width of the insulating layer 200 in an effective amount such that bonding is achieved with the backsheet 141 and a liquid impermeable seal is formed over the at least one central track 4 and the at least portions of the two side tracks 7,8, preferably wherein at a location proximal to the first end 5 of the substrate where the clip-on data processing module 103 is to be connected the adhesive is present only outboard of the at least two side tracks 7,8 and not therebetween such to form a pocket for receiving one or more electrically conducting connection ports 33 of the module 103.

In a preferred embodiment, the first end 5 of the substrate (and/or backsheet 141) corresponds to the front (or belly portion) of the absorbent article and the second end 6 corresponds to the back of the absorbent article.

As shown in FIG. 3 the at least a portion of the wetness sensing tracks 9 that may be alternatingly directly connected and disconnected to the respective side tracks 7,8 along the length L of the substrate 1 is preferably located at positions proximal to the front and/or back (and typically not a central portion positioned therebetween) of the absorbent article. An advantage is that improved wetness monitoring is achieved in the front and back regions of the absorbent article that, together with the sides thereof, is found to be most desirable when detecting risk of leakage.

In an embodiment, the backsheet 141 comprises a slit 15 at a location proximal to the first end 5 of the substrate where the clip-on data processing module 103 is to be connected, said slit being sized such to receive therethrough, typically only, the flexible connection member 31 (typically comprising the connection ports 33) of the clip-on data processing module 103 and wherein, once said clip-on data processing module 103 is connected, said backsheet 141 is interposed between the free end 32 of the flexible connection member 31 and the housing 30 of the clip-on data processing module 103 such that said free end 32 does not come in direct contact with said housing at a position proximal to said free end 32, preferably wherein the housing 30 is positioned on a garment facing side of the backsheet 141 and the free end 32 of the flexible connection member 31 on a body facing side of the backsheet 141. An advantage of this arrangement is that a secure connection may be achieved between the module and the chassis of the article and in particular a very secure electrical connection to the sensor tracks is enabled, whilst it being protected from soiling by internal and/or external elements like dust, exudates, food and the like.

The Clip-on Processing Module

Clip-on processing modules for use herein are generally of the re-fastenable and replaceable kind. What is meant by this is that the modules are adapted to be joined to the absorbent article and subsequently decoupled therefrom once the absorbent article is to be disposed. Thus, the modules are adapted for multiple use and may be connected to a plurality of absorbent articles in sequence (i.e. one after the other) and to the same or different patient/subject. The modules may be cleaned and battery charged in between a plurality of absorbent article changes. The net result is that an efficient, cost-effective and environment-compliant solution is provided.

As explained in more detail in the embodiments herein, the electrical device—so called clip-on module—typically has a part that can be inserted into a pocket of the absorbent article, a second part that remains outside said pocket and a third part that allows bending said device between the first and the second part. The bending part can be a mechanical hinge or flexible element that allows the relative movement between first and second part. It is generally arranged in a way that allows all parts to be cleaned properly after use and avoids gaps that can undesirably facilitate the growth of bacteria and germs. The outer surface material of the modules preferably is selected to provide low friction for the first part that is meant to be inserted, ideally a rounded shape and preferably a soft material for the part that remains outside the pocket.

In an aspect, the disclosure comprises a clip-on data processing module 103 suitable for removable attachment to a chassis of an absorbent article 100 for automatic detection of wetness events therein and more preferably the risk of exudate leakage, the module 103 comprising: a housing 30; and a connection member 31 (the connection member used herein is preferably flexible but it is not necessary to be so, and rather also stiff members are suitable herein) coupled to said housing 30 and having a free end 32 being cantilevered from said housing 30, said end 32 comprising one or more electrically conducting connection ports (also referred to as terminals) 33, wherein the housing 30 comprises therein a data processing system, said data processing system comprising a power source, a processor, and a transmitter; and a motion sensor in electrical communication with at least said processor, the flexible connection member 31 being arranged to fasten to a surface of the absorbent article 100, wherein the absorbent article 100 comprises a plurality of sensor tracks 101, and to electrically connect at least two of said plurality of sensor tracks to said processing system via said one or more electrically conducting connection ports 33.

In an embodiment, the motion sensor (herein also referred to as position sensor) comprises an accelerometer or gyroscope. Preferably, wetness event data and the position data as measured by the module 103 are combined for determination of the saturation level at a specific location of the absorbent article, typically determined respectively for a plurality of local areas of said absorbent article. An advantage of this arrangement is that it more accurately provides warnings to the care givers when the risk of leakage is high thus allowing them to intervene and limit additional cleaning time and costs. As opposed to state of the art systems, the motion sensor described herein is not particularly used to optimize the volume measurement, but rather to combine the position data with the resistive/impedance measured data in order to determine a "local" saturation of the absorbent article, and thereafter preferably predict the risk of leakage in said localized area of the absorbent article.

In an embodiment, the transmitter may be arranged to transmit/forward the data measured to a server or end-user, more preferably said data is transmitted to a server (for example a cloud-based server) wherein further processing of the data (although the processing may also be carried out at least in part also within the processing unit of the clip-on module in the disclosure herein) via for example a mathematical logarithmic model is carried out for determination of patient related information, including risk of leakage within the absorbent article, and the further processed information is then uploaded on a graphical user interface to simply communicate to the care giver a patient status, including providing a warning when the absorbent article is close to a point of leakage (e.g. above a predefined probability threshold such as above 80%, preferably above 85%, more preferably from 88% to 99%). Further embodiments are described in the incontinence management section hereinunder.

In an embodiment, the power source comprised in the housing comprises a battery. The battery and the housing 30 can be disconnected from each other and from the module 103. Whenever the battery has to be replaced e.g. because it has a remaining charging capacity of only about 10% or less left, typically a waring is provided on a user interface to allow a care giver to intervene and replace the battery by simply removing it from the housing 30 and replacing it with another (e.g. fully charged) one, while the measuring electronics (e.g. processor, motion sensor, sensor tracks, and the like) can continue performance under power via a microcharger that is provided and connected thereto during the battery replacement. Time and money is saved whereas the entire module 103 doesn't have to be removed/replaced when only the low or flat battery has to be replaced. Alternatively, the battery may be an integral (non-disconnectable) portion of the unit within the housing.

In an embodiment, the flexible connection member 31 comprises an elastomer, and wherein the one or more electrically conducting connection ports 33 are exposed from said elastomer when the clip-on data processing module 103 is not connected to the chassis of the absorbent article 100. Preferably, the elastomer comprises one or more polymers having a monomer selected from the group consisting of carbon, silicone and mixtures thereof, preferably wherein the elastomer is selected to slide when contacted to PE. Advantages of this arrangement include improved comfort achieved upon connection as well as ease of cleaning after use.

In an embodiment, the housing 30 is covered by an elastomer which can be the same and/or different from that comprised in the flexible connection member 31 and may be of a monolithic structure or different component therefrom. When the clip-on data processing module 103 comprises a display, only the display may be exposed from said elastomer cover. An advantage of this arrangement is improved sealing of components within the housing particularly from liquids such as exudates and/or food.

In an embodiment, the housing 30 and the free end 32 of the flexible connection member 31 comprise a locking member 34 to secure the clip-on data processing module 103 to the absorbent article 100, preferably said locking member consisting of a form-driven locking member or a force-driven locking member and typically arranged to fasten the free end 32 to a position proximal to a portion of the housing 30. Preferably, the locking member comprises a magnet arranged to provide a securing force between the free end 32 and the housing 30 such that said free end 32 adheres directly or indirectly, preferably indirectly via the backsheet 141 of the absorbent article 100, to said housing.

In a preferred embodiment, the flexible connection member 31 has a width that is less than the width w of the insulating layer 200 such that, when connected to the chassis of the absorbent article 100, said connection member slides between the insulating layer 200 and the backsheet 141 typically forming pocket for receiving the same. An advantage of this arrangement is that a secure and protected connection may be achieved in a simple and cost-effective manner, resulting further in an optimum design for readily implementing in fast in-line process of manufacture.

As shown in FIG. 6A to 6C, the clip-on data processing module 103 may further comprise an electronic-ink based display 400 for displaying textual and/or graphical indicia 41 generally relating to the status of said module (such as battery level, wireless connection with the server and/or cloud and the like), patient information, and/or sensing status (such as saturation level of the absorbent article, % risk of leakage at any one point and the like), said display comprising: a layer of electronic ink 42 including a bi-stable non-volatile imaging material disposed between an activation layer (or activation grid) 44 and a transparent electrode layer located above the layer of electronic ink 42, for activating the layer of electronic ink 42 at particular locations to display textual and/or graphical indicia 41 on the surface of the display, wherein the layer of electronic ink 42 does not require electrical power to maintain the indicia 41 visible. An advantage of this arrangement is that visual data is provided for the care giver which allows a status review and/or check directly at the patient alternatively to or in addition to further modules and/or graphical user interfaces, whilst at the same time minimizing the power consumption and overall complexity and size of the clip-on module.

Optionally, the electronic-ink based display 400 further comprises a protective layer 40 positioned such that the layer of electronic ink 42 is between said protective layer 40 and said activation layer 44.

In an embodiment, the display comprises a rigid (e.g. glass-based thin-film-transistor (TFT)) or a flexible (e.g. plastic-based TFT) backplane. Exemplary commercially available displays having rigid backplane for use herein are for example ED013TC1, ED027TC2, ED029TC1, and/or ED035OC1 manufactured and sold by E Ink Corporation, a subsidiary of the YFY Group. Exemplary commercially available displays having flexible backplane for use herein are for example ET011TT2, ET013TT1, ET014TT1, ET029TC1, and/or ET014TT6 manufactured and sold by E Ink Corporation, a subsidiary of the YFY Group.

The Process

The disclosure herein further contemplates a process of making an absorbent article comprising the steps of: providing a liquid impermeable backsheet 141 and applying a plurality of sensor tracks, as described herein; providing an insulating layer 200 having a width w, taken along an axis perpendicular to the longitudinal axis y-y, being less than a width W of said backsheet 141, and typically applying one or more shortening elements 10 thereto, optionally further applying one or more secondary shortening elements 11 thereto; adhering said insulating layer 200 to said backsheet 141, said insulating layer being sized and positioned to cover the at least one central track 4 and optionally a portion of the at least two side tracks 7,8, to provide a laminated substrate; providing an absorbent core 143 comprising absorbent material; providing a liquid permeable topsheet 142; and sandwiching the absorbent core 143 between said backsheet 141 and said topsheet 142. Preferably, the sensor tracks are in the form of an electrically conductive ink and the application step comprises the printing thereof onto the backsheet 141, preferably wherein the shortening elements 10 and the secondary shortening elements 11 are in the form of an electrically conductive ink and the application step comprises the printing thereof onto the insulating layer 200 or backsheet 141.

In an alternative embodiment, when using a registered sensor design as explained herein above with reference to FIGS. 7-8, similar process steps to the above may be carried out except that the shortening elements 10 and/or secondary shortening elements 11 are not applied to the insulating layer 200 but rather directly to the substrate 1 (typically being the backsheet 141). Moreover, the process generally comprises the step of detecting registered marks 300 to trigger accurate cutting of the substrate 1 (or the assembled/laminated continuous absorbent article) into a plurality discrete absorbent articles.

In a preferred embodiment the width w of the insulating layer 200 is less than the width W of the backsheet 141 (and/or substrate 1), preferably is less than 0.5W, more preferably from 0.05W to 0.35W, even more preferably from 0.08W to 0.30W, most preferably from 0.1W to 0.2W.

In an embodiment, the layers referred to herein above (i.e. at least the backsheet 141 and the insulating layer) are in the form of continuous webs and/or films that are first printed with conductive ink in the pattern described above (sensor tracks and shortening elements respectively) prior to being laminated together and subsequently cut into individual absorbent articles.

In an embodiment, the insulating layer 200 is adhered to the backsheet 141 by an adhesive and/or mechanical bonding, wherein the mechanical bonding is preferably selected from ultrasonic bonding, thermal bonding, and combinations thereof. In a preferred embodiment, the adhesive and/or mechanical bonding is applied across a length and width of the insulating layer 200 in an effective amount such that bonding is achieved with the backsheet 141 and a liquid impermeable seal is formed providing a barrier to exudates expelled by a subject, when wearing the absorbent article 100, from coming into direct contact with the at least one central track 4 and the at least two side tracks 7,8, preferably wherein at a location proximal to the first end 5 of the backsheet 141 where the clip-on data processing module 103 is to be connected the adhesive is present only outboard of the at least two side tracks 7,8 and not therebetween such to form a pocket for receiving an electrically conducting portion of said module 103.

The Incontinence Management System

In accordance to an aspect of the disclosure, an incontinence management system is provided for managing raw data generated by the modules described herein in cooperation with the sensor tracks described above and located on a substrate of respective absorbent articles, and adapted to process the raw data to processed data, transfer the raw data and/or the processed data over a network, and link the raw data and/or the processed data with person data of a given patient or individual. The management system may comprise a module 103 comprising a transmitter as described herein above for delivering the raw data (although processing may also take place within the unit), a cloud server for processing the raw data to processed data, preferably by applying a mathematical logarithmic model, and a client application or graphical user interface for linking the raw data and the processed data with person data. The management system may optionally further comprise one or more docking stations for initializing the modules 103 for first time use, the latter may also be done via a portable device such as a smart phone and/or tablet.

In a preferred embodiment, the network herein is a wireless network being a sub-Ghz wireless network (i.e. having data rates of from 20 kbit/s (868 MHz band) to 250 kbit/s (2.4 GHz band) such as Zigbee) which is preferred over Wi-Fi that typically operates at higher data rates (from 2.4 Ghz to 5 Ghz). An advantage of this arrangement is to provide a large broadcasting distance, low energy consumption and to remain independent from any existing wifi networks that for example may be in place at a given institution or elderly home, so that the system described herein does not need to share bandwidth with other applications thus improving reliability and consistency of data acquisition and processing.

In an embodiment, the disclosure further contemplates an incontinence management system for managing the measured or captured data (by the absorbent articles and modules described herein), thereby using a network wherein the data can be transmitted, for example anonymized patient data (typically of relevance for instance in a nursing home or residential care institution and the like). The measured data or sensor data as used herein is also referred to as raw data.

The clip-on modules described herein may comprise a unique identifier via its media access control (MAC) address which may be linked to an individual or patient. Preferably, the unique identifier may be comprised in the form of indicia (e.g. a QR-code) applied to an external surface of the clip-on modules that may be scanned by a linking device (such as smart phone or tablet) for linking a given module to a given individual and/or patient. The linking may alternatively be done manually by inputting the identifier number of a given module to the linking device by typing the same.

In an embodiment, a plurality of modules as described herein are connected to the cloud where the sensor data is linked with an individual or patient, preferably anonymously via numerical identifiers randomly generated for each individual or patient. Preferably, the raw data is processed within the cloud wherein one or more mathematical models may be applied to further compute and predict a plurality of wetness status, pathological status, and/or physiological status for each individual/patient. Referring to the application within a nursing home for instance, a linking dock may be provided locally in the nursing home, and acting as network access point and server.

In an embodiment the network is a wireless network, e.g. a local wireless network such as wireless local area network (WLAN) (typically using WiFi™) and/or Bluetooth™ for the wireless connection. Most preferred wireless network however remains Zigbee as described above, and herein after embodiments that specifically refer to wifi can be, and are preferably implemented, with Zigbee. Regarding the use of a unique identifier, a service set identifier (SSID) is then for instance used over the WLAN and may be provided by the linking dock. The modules may be linked with the linking dock prior to each module being installed. Moreover, the linking dock may provide an initialization and/or setting startup/installation of the module to pre-set and/or activate it for use, within this initialization the module is provided with the unique anonymous individual/patient number, stores this number and relates this number (typically through a database) with real patient identification such as a person's name for example. A client application may further be part of the network, and may be directly linked with the linking dock, and hence generally a nursing home patient dashboard. Via the client application, the linking dock or nursing home dashboard is able to indicate which module is linked with a particular patient, whereas the real individual/patient identification is stored in a separate database that is linked with the linking dock. Real patient information can be displayed by the client application such as for example a tablet or smart phone. Such information includes for instance not only a real person's identification, but also processed data or computed information from the cloud.

In an embodiment, the measured data is captured by means of the module described herein (typically by receiving and processing resistive and/or capacitance signals through the plurality of sensor tracks comprised in a substrate of the absorbent article as described herein). The measured data (comprising raw data) is subsequently transferred to the cloud by means of a wireless data transfer (typically via the transmitter present the modules described herein above). Preferably, the measured data is pre-processed by the processor comprised in the module and subsequently transmitted to the cloud for application of the mathematical model used to predict for example the saturation level of the absorbent article and/or the risk of leakage. An advantage of the latter arrangement is that the heavy signal processing and computing is decoupled from the actual hardware connected to the absorbent article, thus allowing reduced power consumption and device complexity which in turns makes for simpler large scale manufacturing as well as reduced module size for comfort of wear and handling.

In an embodiment, the modules are distributed and installed to the absorbent articles (by connecting to the chassis thereof as described herein) of the corresponding individuals or patients. Each module may comprise a visual identification number, e.g. between 1 and 999 typically displayed on a portion of the display described herein above. This may be useful when replacing one module with another for servicing, cleaning and the like for a given patient, for example when replacing a module the new module may acquire the identification number of the replaced module either manually by inputting it directly to the module or preferably automatically via the client application or graphical user interface (GUI). In parallel, the GUI may also inform the cloud server that the unique identifier is now linked to the newly replaced module.

In an embodiment, the raw data is communicated to the cloud server, which recognizes the identifier of the module and links this data to a unique anonymous identifier of the patient. The cloud server processes, computes or calculates useful information from this raw data and makes such information accessible in graphical representation for different end-users or care givers using a GUI or client application.

Preferably, the end-users such as for instance care givers or other nursing home personnel can connect with the cloud and extract e.g. the needed information for their typical department. The data from the cloud is still anonymous and the unique anonymous identifiers have to be replaced with real names and information. The client application or GUI accesses the linking dock server such that the useful information or other cloud data is linked to a real name of an individual or patient. Thus, the module delivers raw data linked to a unique identifier, such as e.g. a MAC address. The cloud server processes such data and links such unique identifier to a unique person or patient number. The processed data can now be accessed by a client application. The client application replaces the unique person or patient number with a real person or patient identification, including for example information regarding room number, age, and name.

It is supposed that the present invention is not restricted to any form of realization described previously and that some modifications can be added to the presented example of fabrication without reappraisal of the appended claims.

The invention claimed is:

1. An absorbent article (100) suitable for detecting a wetness event therein and/or risk of exudate leakage therefrom, said absorbent article comprising:
   a liquid impermeable backsheet (141);
   a liquid permeable topsheet (142);
   an absorbent core (143) interposed between said backsheet (141) and topsheet (142),
   a clip-on data processing module (103) that is capable of being removed;
   and a substrate (1) comprising a first surface (2) proximal to a body facing side of the absorbent article (100) and a second surface (3) opposite said first surface (2) and arranged proximal to a garment facing side of said absorbent article (100), said substrate (1) comprising a plurality of sensor tracks (101) disposed on said first surface (2) wherein said sensor tracks (101) are in electrical communication with a plurality of exposed electrically conductive terminals (33) of the clip-on data processing module (103) when connected at a position proximal to a first end (5) of the substrate (1) such to form a closed electrical circuit,
   characterised in that said substrate (1) comprises one or more slits (15) and an insulating layer (200) placed over said first surface (2) to sandwich at least a portion of said sensor tracks (101) therebetween, and in that a pocket (16) is formed between said first surface (2) and said insulating layer (200) at least proximal to said first end (5), said pocket (16) being in fluid communication with said slit(s) (15) and arranged to retain at least a portion of said clip-on data processing module (103) therein, wherein said portion comprises the exposed electrically conductive terminals (33), and wherein said substrate (1) consists of the liquid impermeable backsheet (141) and said insulating layer (200) is a non-conductive film, and wherein the pocket (16) is delimited along a garment facing outer surface of the pocket (16) by the garment facing surface of the substrate (1) and along a skin facing inner surface of the pocket (16) by the insulating layer (200), and along at least the longitudinally extending dimensions of a perimeter of the pocket (16) by a bonding seal (22) such that the pocket remains impermeable to exudates.

2. An absorbent article according to claim 1 wherein said pocket is delimited along the perimeter of the pocket (16) by the bonding seal (22).

3. An absorbent article according to claim 1 wherein the pocket (16) is positioned over at least a portion of the absorbent core (143) with the core (143) being interposed between said pocket (16) and the skin of a subject when the absorbent article is worn such that when the clip-on data processing module (103) is inserted into the pocket (16) the absorbent core (143) provides a cushioning layer between said module (103) and said skin of the subject.

4. An absorbent article according to claim 1, wherein the absorbent article is a disposable diaper, pad or pant.

5. An absorbent article (100) according to claim 1 wherein the sensor tracks (101) comprise an electrically conductive material, and are printed sensor tracks, and wherein the printed sensor tracks (101) comprise a carbon-based ink and/or a conductive polymer-based ink, wherein the carbon-based ink comprises a conductive compound selected from the group consisting of graphene, graphite, nano-carbon-tubes and mixtures thereof, and wherein the conductive polymer-based ink comprises a conductive compound selected from the group consisting of polyacetylene, polypyrrole, polyaniline and copolymers thereof.

6. An absorbent article (100) according to claim 1 wherein the insulating layer (200) is liquid impermeable, and the plurality of sensor tracks (101) comprising:
   at least one central track (4) extending parallel to length (L) of the substrate and parallel to a longitudinal axis (y-y) crossing a first end (5) and a second end (6) of the substrate (1);
   at least two side tracks (7,8) extending parallel to the central track (4) along at least a portion of the length (L) and oppositely arranged such that the central track (4) extends substantially therebetween; and
   wetness sensing tracks (9) extending outboard of said two side tracks (7,8) and/or central track (4),
   wherein said central track (4), said side tracks (7,8), and said wetness sensing tracks (9) are in electrical communication via one or more shortening elements (10) positioned proximal to said second end (6) and distal from said first end (5), and wherein said insulating layer (200) is sized to cover the at least one central track (4) and at least a portion of the side tracks (7,8), said insulating layer (200) adapted to provide a seal and/or barrier to liquid from coming into contact with said central track (4) and said side tracks (7,8).

7. An absorbent article (100) according to claim 1 wherein the slit(s) (15) comprises one or more insertion indicators arranged to provide an indication to a user of the insertion position of the clip-on processing module (103) therethrough, wherein said insertion indicator is selected from the group consisting of:
   indicia positioned on a surface of the insulating layer (200) that faces said substrate such that said indicia is seen through said slit(s) (15);
   indicia positioned on the garment facing surface of said substrate (1) such that said indicia surrounds a perimeter of said slit(s) (15);
   a patch (17) comprising indicia joinable to the garment facing surface of said substrate (1) such that said patch surrounds a perimeter of said slit(s) (15); and combinations thereof.

8. An absorbent article (100) according to claim 1 wherein a reinforcement layer (18) is joined to a garment facing surface of said substrate (1) along a perimeter of the slit(s) (15) and at least a portion of said surface outboard of said perimeter, and wherein said slit(s) (15) forms an opening free of said reinforcement layer (18).

9. An absorbent article (100) according to claim 8 wherein said reinforcement layer (18) is laminated over the entire garment facing surface of said substrate (1) except the opening; or is laminated only over a central portion of said garment facing surface of said substrate (1) along a length (L) of said substrate (1) except said opening; or is laminated only over an area of said garment facing surface immediately adjacent to the perimeter of said slit(s) (15) except said opening.

10. An absorbent article (100) according to claim 8 wherein the reinforcement layer (18) is in the form of a patch.

11. An absorbent article (100) according to claim 1 wherein the slit(s) (15) is in the form of a straight linear cut, square cut, square cut with rounded edges, oval cut, rounded rhombus cut, mouth-shaped cut, or combination thereof.

12. An absorbent article (100) according to claim 1 wherein the slit(s) (15) is rounded such that a flap (26) is formed having a flap length ($L_f$) arranged to be lifted with a finger for insertion of the unit (103).

13. An absorbent article (100) according to claim 1 wherein the slit(s) (15) is free of sharp edges having a notch radius (R) of less than 1 mm.

14. An absorbent article (100) according to claim 1 wherein the plurality of sensor tracks (101) are divided into a right half circuit (19) and left half circuit (20) symmetrically disposed about a longitudinal axis (y-y), and comprising at least two central tracks (4) extending parallel to each other along a length (L) of the substrate (1) each being directly connected to said right half circuit (19) or left half circuit (20), and wherein either said right half (19) is in electrical communication with said left half (20) only when the clip-on processing module (103) is connected thereto, or wherein said right half (19) and said left half (20) are not in electrical communication with each other when the clip-on processing module (103) is connected and rather remain two independent electrical circuits.

15. An absorbent article (100) according to claim 1 wherein the plurality of sensor tracks (101) are divided into a front half circuit (27) and rear half circuit (28) symmetrically disposed about an axis perpendicular to the longitudinal axis (y-y) and comprising at least two central tracks (4) extending parallel to each other along a length (L) of the substrate (1) each being directly connected to said front half circuit (27) and/or rear half circuit (28), and wherein either said front half (27) is in electrical communication with said rear half (28) only when the clip-on processing module (103) is connected thereto, or wherein said front half (27) and said rear half (28) are not in electrical communication with each other when the clip-on processing module (103) is connected and rather remain as two independent electrical circuits.

16. An absorbent article (100) according to claim 5 wherein the conductive polymer-based ink comprises a conductive compound selected from the group consisting of poly(pyrrole)s (PPY), polyanilines (PANI), poly(thiophene)s (PT), poly(p-phenylene sulfide) (PPS), poly(p-phenylene) (PPP), Poly(acetylene)s (PAC), Poly(p-phenylene vinylene) (PPV), poly(3,4-ethylenedioxythiophene) (PEDOT), and mixtures thereof.

17. An absorbent article (100) according to claim 5 wherein the conductive polymer-based ink comprises poly (3,4-ethylenedioxythiophene) polystyrene sulfonate (PEDOT:PSS).

18. An absorbent article (100) to claim 6 wherein the wetness sensing tracks (9) remain exposed and are not covered by said insulating layer (200).

19. An absorbent article (100) according to claim 10 wherein said patch has a color and/or texture that is visually or tactilely different from the color and/or texture of the garment facing surface of said substrate (1).

20. An absorbent article (100) according to claim 11 wherein the slit(s) (15) is in the form of a oval cut, rounded rhombus cut and/or mouth-shaped cut.

21. An absorbent article according to claim 6 wherein the number of said terminals (33) is at least the same as the number of said central and side tracks (4,7,8).

* * * * *